United States Patent
Hirono

(10) Patent No.: US 11,241,146 B2
(45) Date of Patent: Feb. 8, 2022

(54) ENDOSCOPE

(71) Applicant: OLYMPUS CORPORATION, Tokyo (JP)

(72) Inventor: Takayoshi Hirono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 120 days.

(21) Appl. No.: 16/738,493

(22) Filed: Jan. 9, 2020

(65) Prior Publication Data

US 2020/0146539 A1 May 14, 2020

Related U.S. Application Data

(63) Continuation of application No. PCT/JP2018/020438, filed on May 29, 2018.

(30) Foreign Application Priority Data

Jul. 13, 2017 (JP) .............................. JP2017-137236

(51) Int. Cl.
*A61B 1/00* (2006.01)
*G02B 23/24* (2006.01)

(52) U.S. Cl.
CPC ...... *A61B 1/00183* (2013.01); *A61B 1/00096* (2013.01); *G02B 23/2423* (2013.01)

(58) Field of Classification Search
CPC ............. A61B 1/00096; A61B 1/0057; A61B 1/00163; A61B 1/00183; A61B 1/00064;
(Continued)

(56) References Cited

U.S. PATENT DOCUMENTS 5,842,972 A * 12/1998 Wulfsberg ......... A61B 1/00188
600/167
6,371,909 B1 * 4/2002 Hoeg .................. A61B 1/00096
600/112
(Continued)

FOREIGN PATENT DOCUMENTS

EP 1 690 492 A1 8/2006
EP 3 216 383 A1 9/2017
(Continued)

OTHER PUBLICATIONS

International Search Report dated Aug. 14, 2018 received in PCT/JP2018/020438.

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

An endoscope includes a prism disposed in a distal end portion of an insertion section and configured to change a direction of a field of view in an upward, downward, leftward, or rightward direction, an operation lever disposed in an operation section, being turnable from a neutral position around a third axis and a fourth axis that are perpendicular to each other, and including a second longitudinal axis, a cylindrical member disposed such that turning around a fourth axis of the lever is transmitted and configured to turn around the fourth axis by inclining the operation lever, a transmission wire configured to transmit turning around a first axis to the prism in response to an inclination operation around the third axis of the lever, and gears configured to transmit turning around a second axis to the prism in response to a turning operation around the fourth axis.

20 Claims, 28 Drawing Sheets

(58) Field of Classification Search
CPC . A61B 1/00177; A61B 1/00181; A61B 1/042; A61B 1/0052; G02B 23/26; G02B 23/2423
USPC .......................................................... 600/173
See application file for complete search history.

(56) References Cited

U.S. PATENT DOCUMENTS

| | | |
|---|---|---|
| 2001/0018553 A1 | 8/2001 | Krattiger et al. |
| 2002/0099263 A1* | 7/2002 | Hale .................. A61B 1/00179 600/117 |
| 2004/0266574 A1* | 12/2004 | Jinno ................. A61B 17/0469 474/153 |
| 2005/0177026 A1* | 8/2005 | Hoeg ................... A61B 1/0051 600/173 |
| 2006/0206006 A1 | 9/2006 | Schara et al. |
| 2012/0165605 A1* | 6/2012 | Yamazaki .......... G02B 23/2476 600/106 |
| 2014/0121459 A1* | 5/2014 | Hoeg ................. A61B 1/00174 600/109 |
| 2016/0331212 A1 | 11/2016 | Yasunaga |
| 2017/0280980 A1 | 10/2017 | Yasunaga et al. |

FOREIGN PATENT DOCUMENTS

| | | |
|---|---|---|
| JP | 2006-223866 A | 8/2006 |
| JP | 2010-029658 A | 2/2010 |
| JP | 5932165 B | 6/2016 |
| WO | 2016/035359 A1 | 3/2016 |
| WO | WO2016035359 * | 3/2016 |
| WO | 2017/010198 A1 | 1/2017 |

* cited by examiner

ENDOSCOPE

CROSS REFERENCE TO RELATED APPLICATION

This application is a continuation application of PCT/JP2018/020438 filed on May 29, 2018 and claims benefit of Japanese Application No. 2017-137236 filed in Japan on Jul. 13, 2017, the entire contents of which are incorporated herein by this reference.

BACKGROUND OF THE INVENTION

1. Field of the Invention

The present invention relates to a field of view direction variable endoscope, and more particularly to an endoscope that changes a direction of a field of view by moving an optical element provided in a distal end portion of an insertion section.

2. Description of the Related Art

To observe a portion which is not easily observed, such as an inside of a living body or an inside of a structure, an endoscope that can be introduced into the living body or the structure from outside and picks up an optical image has been used in a medical field or an industrial field, for example.

Examples of the endoscope include an endoscope including a flexible insertion section used for inspection and treatment of a digestive tract and an endoscope including a rigid insertion section used for a surgical operation.

Particularly, the endoscope including the rigid insertion section is referred to as a rigid endoscope, a laparoscope, a nephroscope, or the like. For example, a turning prism endoscope that turns and inclines a prism as an optical element at its distal end to vibrate an optical axis and can change a field of view (an angle of squint) is known, as disclosed in Japanese Patent Application Laid-Open Publication No. 2010-29658.

For a problem that two different operations are required to be combined for a field of view operation of an endoscope in Japanese Patent Application Laid-Open Publication No. 2010-29658, Japanese Patent No. 5932165 (International Publication No. WO2016/035359) proposes a turning prism endoscope that can intuitively change a field of view (an angle of squint) by turning and inclining a prism as an optical element at its distal end upward, downward, leftward, and rightward using one operation system.

SUMMARY OF THE INVENTION

An endoscope according to an aspect of the present invention includes a rigid insertion section including a longitudinal axis, an operation section consecutively provided at a proximal end of the insertion section, an optical element disposed turnably around a first axis perpendicular to the longitudinal axis and a second axis parallel to the longitudinal axis in a distal end portion of the insertion section and configured to change a direction of a field of view in an upward, downward, leftward, or rightward direction, an operating member disposed in the operation section, the operating member being turnable from a neutral position around a third axis and a fourth axis that are perpendicular to each other, and including a second longitudinal axis, a turning member including the fourth axis provided parallel to the second longitudinal axis at the neutral position of the operating member, disposed such that turning around the fourth axis of the operating member is transmitted, and configured to turn around the fourth axis by inclining the operating member, a first transmitting member to which the optical element and the operating member are connected and configured to transmit turning around the first axis to the optical element in response to an inclination operation around the third axis of the operating member, and a second transmitting member including a proximal end portion connected to the turning member and configured to transmit turning around the second axis to the optical element in response to a turning operation around the fourth axis of the operating member with the operating member turned around the third axis from the neutral position.

DETAILED DESCRIPTION OF THE PREFERRED EMBODIMENTS

Figure 1:
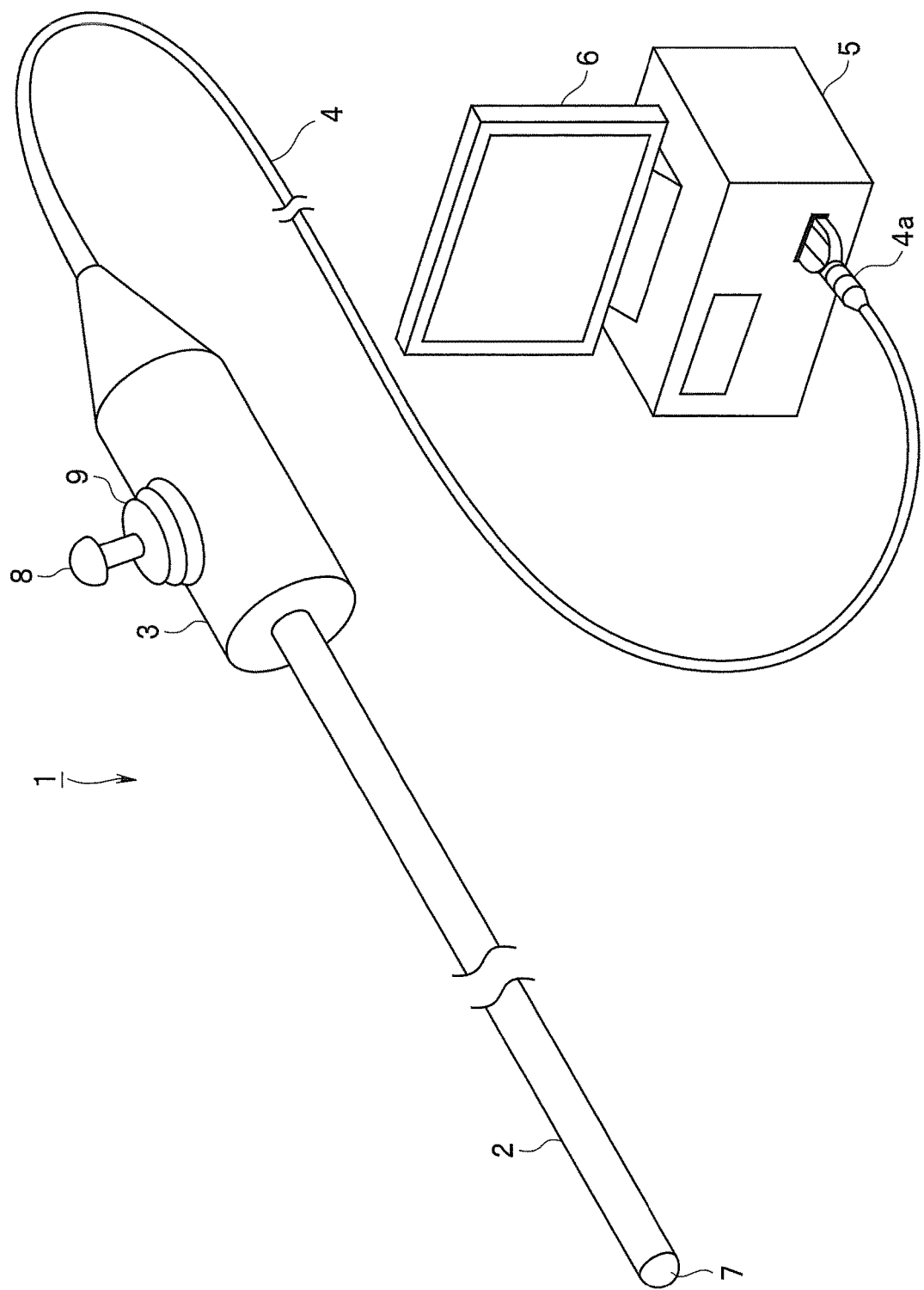
FIG. 1 is a perspective view illustrating an entire configuration of an endoscope according to a first embodiment.

Preferred embodiments of the present invention will be described below with reference to the drawings. In the drawings used for the following description, scales are made to respectively differ for components to make each of the components have a recognizable size on the drawings. The present invention is not limited to only the number of the components described in the drawings, a shape of each of the components, a ratio of the respective sizes of the components, and a relative positional relationship among the components. In the following description, an up-and-down direction viewed toward a paper plane of the drawing may be described as an upper side and a lower side of each of the components.

First Embodiment

Figure 2:
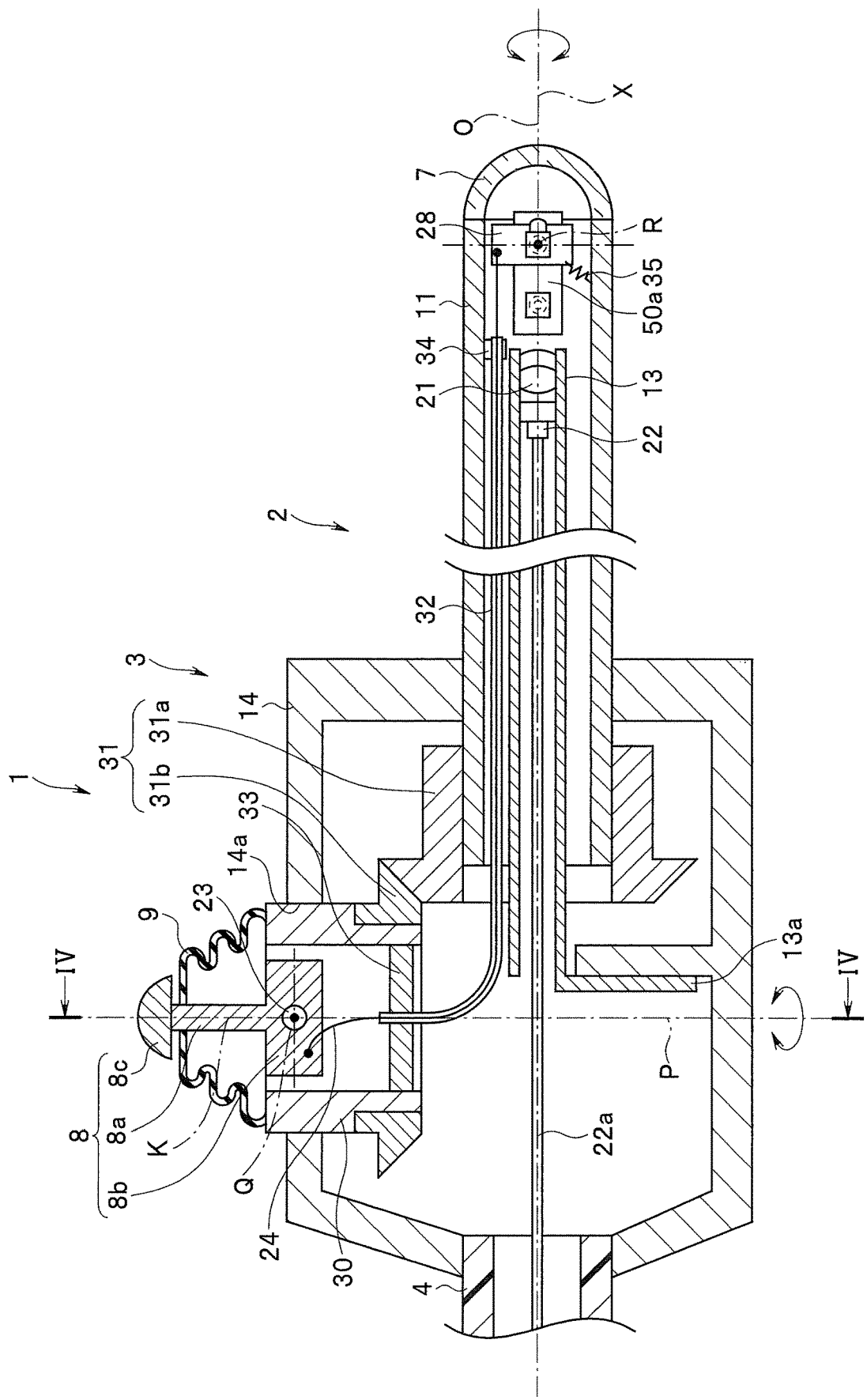
FIG. 2 is a cross-sectional view illustrating a configuration of the endoscope according to the first embodiment.
Figure 3:
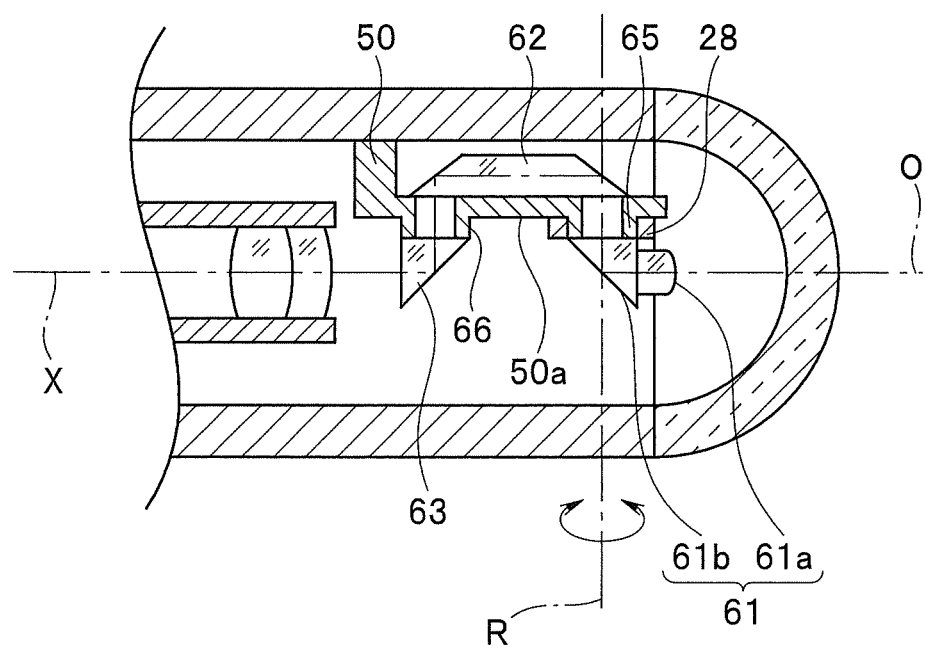
FIG. 3 is a cross-sectional view illustrating a configuration of the endoscope according to the first embodiment.
Figure 4:
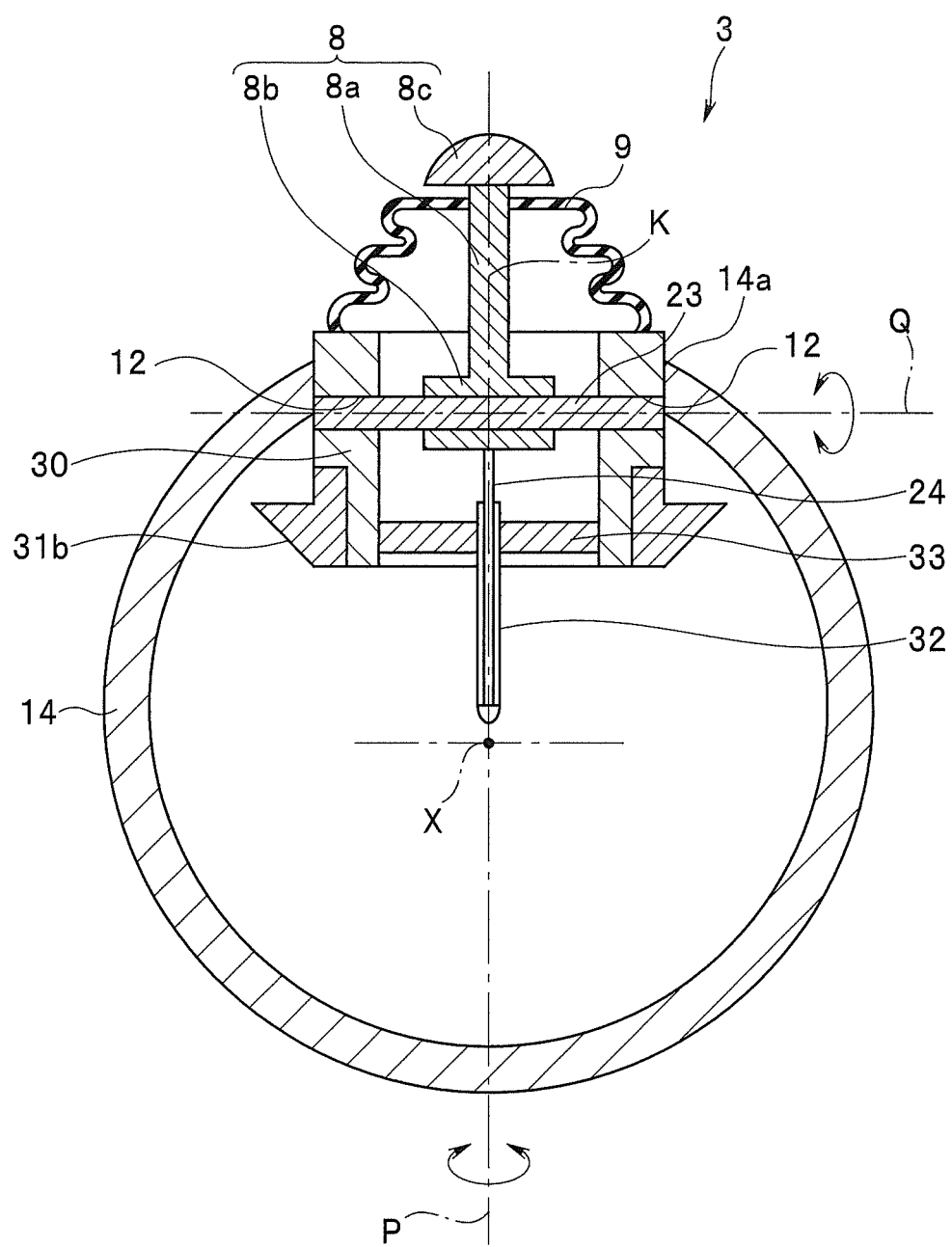
FIG. 4 is a cross-sectional view taken along a line IV-IV illustrated in FIG. 2 according to the first embodiment.
Figure 5:
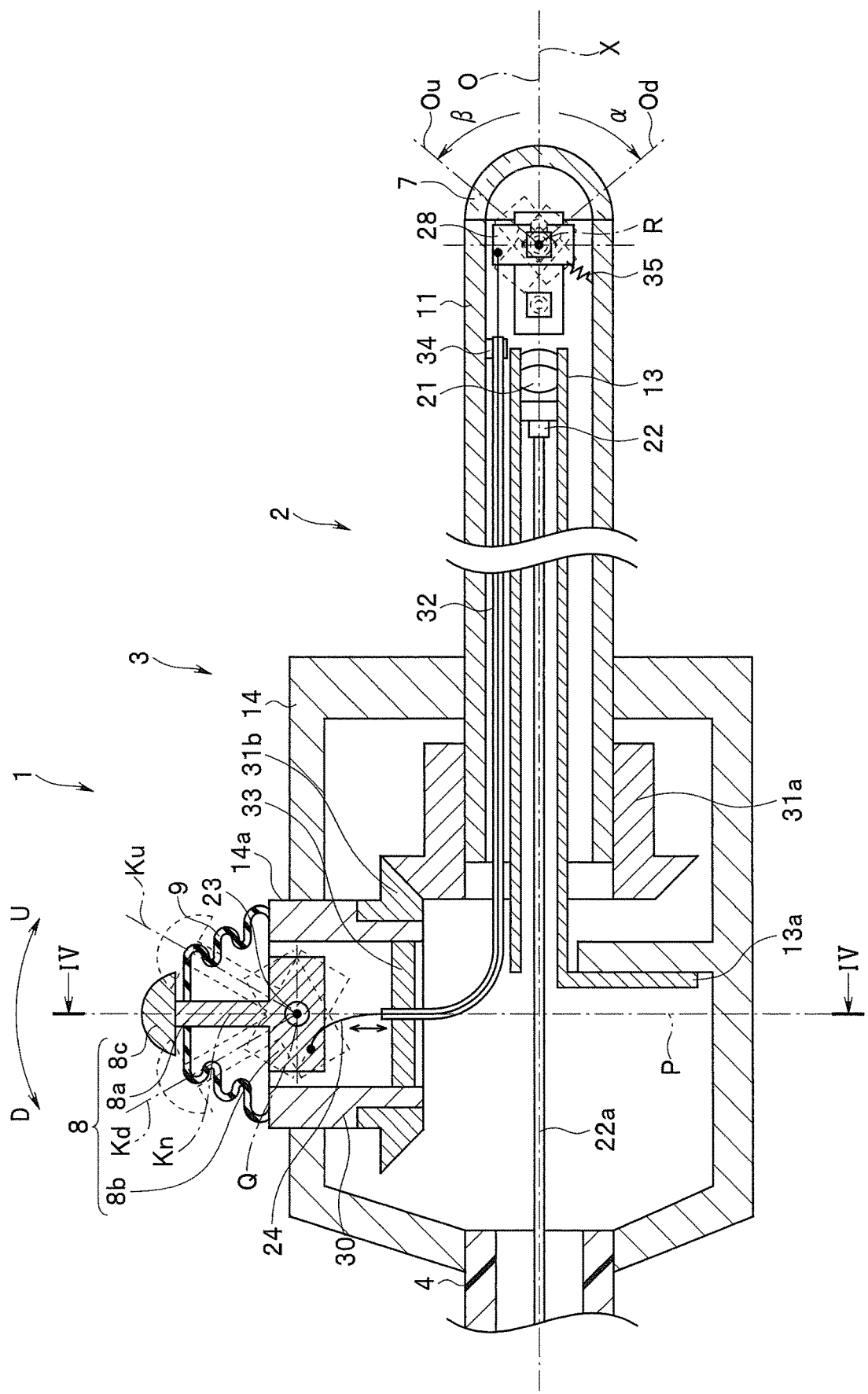
FIG. 5 is a cross-sectional view for describing an operation of the endoscope according to the first embodiment.

An endoscope according to a first embodiment of the present invention will be described below. FIG. 1 is a perspective view illustrating an entire configuration of the endoscope according to the first embodiment, FIG. 2 is a cross-sectional view illustrating a configuration of the endoscope according to the first embodiment, FIG. 3 is a cross-sectional view in a vertical direction of FIG. 2 illustrating a configuration of a distal end portion of the endoscope according to the first embodiment, FIG. 4 is a cross-sectional view taken along a line IV-IV illustrated in FIG. 2, FIG. 5 is a cross-sectional view for describing an operation of the endoscope according to the first embodiment, and FIGS. 6, 7, 8, and 9 are each a perspective view of an endoscope for describing a function of the endoscope according to the first embodiment.

An example of a configuration of an endoscope 1 according to the first embodiment of the present invention will be described with reference to FIG. 1.

The endoscope 1 according to the present embodiment is medical equipment that can be introduced into a subject such as a human body and is particularly used for surgery or inspecting a urinary organ or the like, and is configured to optically pick up an image of a predetermined observation site within the subject.

The subject into which the endoscope 1 is introduced is not limited to a human body, but may be another living body or may be an artifact such as a machine or a building.

The endoscope 1 mainly includes a rigid insertion section 2 to be introduced into the subject, an operation section 3 positioned at a proximal end of the insertion section 2, and a universal cord 4 extending from a proximal end portion of the operation section 3. In other words, the endoscope 1 includes a rigid insertion section 2 having a longitudinal axis and an operation section 3 consecutively provided at a proximal end of the insertion section 2. Note that the endoscope 1 has a form of a so-called rigid endoscope, laparoscope, nephroscope, or the like not including a site having flexibility in the insertion section 2.

The universal cord 4 has an endoscope connector 4a to be connected to an external apparatus 5 such as a video processor provided in its proximal end portion.

The external apparatus 5 is provided with an image processing section. The image processing section generates a video signal based on an image pickup device output signal outputted from an image pickup device, described below, and outputs the generated video signal to the image display section 6 as a monitor. In other words, in the present embodiment, an optical image (endoscope image) picked up by the image pickup device is displayed as a video on the image display section 6.

The insertion section 2 in the endoscope 1 has a dome-shaped cover glass 7 as an observation window provided at its distal end.

The operation section 3 in the endoscope 1 is provided with a rubber boot 9 as a cover body that has an operation lever 8 as an operating member of a so-called joystick type disposed at its central top and covers a protruding root portion of the operation lever 8.

Then, an internal configuration of the endoscope 1 will be described in detail below with reference to FIGS. 2 to 4.

As illustrated in FIG. 2, the insertion section 2 in the endoscope 1 includes an exterior tube 11 as an insertion pipe having its distal end sealed with the dome-shaped cover glass 7. An image pickup system holding barrel 13 is disposed within the exterior tube 11.

A proximal end side of the exterior tube 11 is fitted and inserted into an operation section frame body 14 constituting an exterior of the operation section 3, and is connected to the operation section frame body 14 turnably around a central axis X in a state where movement along the central axis X of the exterior tube 11 is restricted. A sliding contact portion between the operation section frame body 14 and the exterior tube 11 is kept watertight using an O-shaped ring, not illustrated. A bevel gear 31a as a transmitting member is integrally fixed to a proximal end portion of the exterior tube 11 coaxially with the central axis X as a second axis. Note that the bevel gear 31a meshes with a bevel gear 31b, described below. The bevel gears 31a and 31b constitute a gear section 31 as a second transmitting member. The exterior tube 11 may be connected to the operation section frame body 14 via a bearing or the like to easily turn around its longitudinal axis.

The operation section frame body 14 has a substantially cylindrical shape, and has an opening section 14a formed at its top center. A cylindrical member 30 as a cylinder-shaped member is fitted and inserted into the opening section 14a, and is connected to the operation section frame body 14 turnably around a turning axis P as a fourth axis perpendicular to the central axis X in a state where movement along the turning axis P is restricted. A sliding contact portion between the operation section frame body 14 and the cylindrical member 30 is kept watertight using an O-shaped ring, not illustrated. Note that the cylindrical member 30 as a turning member may be connected to the operation section frame body 14 via a bearing or the like to easily turn around the turning axis P.

The bevel gear 31b is integrally fixed to a bottom of the cylindrical member 30, and the bevel gears 31a and 31b mesh with each other at a turning transmission ratio of 1:1. Note that the above-described bevel gears 31a and 31b may be the same.

Note that although two bevel gears are used to convert turning of the cylindrical member 30 into turning of the exterior tube 11, a conversion mechanism using a spur gear may be used.

The operation lever 8 is provided with a block-shaped shaft receiving section 8b as a shaft receiving section disposed at a proximal end of an operation rod 8a. A shaft 23 as a turning shaft is inserted into and fixed to the shaft receiving section 8b by press-fitting or the like. In FIG. 2, K is a longitudinal axis of the operation rod 8a, and is coaxial with and parallel to the turning axis P in FIG. 2.

The shaft 23 has both its end portions inserted into a shaft holding hole 12 formed in the cylindrical member 30, and is turnably held around the turning axis Q in a state where movement along a turning axis Q as a third axis defined, i.e., provided by the shaft holding hole 12 is restricted. The turning axis Q is perpendicular to the turning axis P, and the shaft 23 is turnable around the turning axis P while such an orthogonal state is kept.

A turning angle around the turning axis Q of the operation lever 8 is less than 180 degrees.

Note that one end of a transmission wire 24 as a first transmitting member is fixed to a portion on the side of the universal cord 4 of the shaft receiving section 8b in the operation lever 8 (on the left side of the turning axis P in FIG. 2).

The rubber boot 9 is fixed to an upper surface of the cylindrical member 30 and a side surface of the operation rod 8a while being kept watertight, and is deformed as the operation lever 8 is inclined around the turning axis Q.

A knob section 8c in the operation lever 8 is turnably connected around the longitudinal axis K to an end portion, on the opposite side to the shaft receiving section 8b, of the operation rod 8a in a state where movement along a longitudinal axis K of the operation rod 8a is restricted. Note that the knob section 8c may be integrally fixed to the operation rod 8a.

The image pickup system holding barrel 13 holds a plurality of, here two image-forming lenses 21 as an image pickup optical system inside its distal end, and an image pickup device 22 is disposed at an image-forming position of a subject image by the two image-forming lenses 21.

Note that the image pickup device 22 is a very small electronic component. The image pickup device 22 has a plurality of elements each configured to output an electrical signal corresponding to light indicated by a shooting optical axis O to be incident at a predetermined timing arranged in its planar light receiving section, and formats generally referred to as a CCD (charge-coupled device) image sensor, a CMOS (complementary metal oxide semiconductor) image sensor, and the like, or various types of other formats, for example, are applied to the image pickup device 22. The image pickup device 22 is connected to a circuit board, not illustrated, for example.

An image pickup cable 22a is connected to the image pickup device 22. The image pickup cable 22a is inserted into the image pickup system holding barrel 13, and is inserted into the universal cord 4 disposed at a rear end of the operation section frame body 14 via the operation section frame body 14 in the operation section 3, to be connected to the endoscope connector 4a illustrated in FIG. 1.

The image pickup system holding barrel 13 is provided with a fixing plate section 13a extending downward at its proximal end, and the fixing plate section 13a is fixed to a lower inner surface on the side of a distal end of the operation section frame body 14 with a screw, not illustrated, for example.

Note that the exterior tube 11 is disposed such that the central axis X and a center of the image pickup system holding barrel 13 match each other.

The transmission wire 24 extends into the exterior tube 11 on the side of the operation section 3, and is connected to an upper corner portion of a plate-shaped optical element holding member 28, as illustrated in FIG. 2, at the other end on the side of the insertion section 2.

The transmission wire 24 is inserted into a coil 32, and can advance and retreat within the coil 32 in a stable shape because both ends of the coil 32 are respectively fixed by a coil fixing member 33 in the cylindrical member 30 and fixed by a coil fixing member 34 fixed to an inner peripheral surface of the exterior tube 11 in a distal end portion of the exterior tube 11.

A support base 50 having a substantially L shape in cross section is fixed to an inner peripheral surface of the distal end portion of the exterior tube 11, the support base 50 protrudes along the central axis X toward one surface of a plate-shaped extension section 50a extending along the central axis X in the support base 50, and a first cylindrical section 65 and a second cylindrical section 66 each having a hole portion formed therein are provided side by side in a back-and-forth direction.

A hole portion formed in a central portion of the optical element holding member 28 is externally inserted into the first cylindrical section 65 in the support base 50, and the optical element holding member 28 is turnably fitted in the first cylindrical section 65. In the drawings, R is a turning axis defined by the above-described first cylindrical section 65, and is perpendicular to the above-described central axis X.

A first prism 61 including an objective lens 61a and a triangular prism 61b integrated with each other is fixed to the optical element holding member 28. Note that one end of the above-described transmission wire 24 is connected to a portion above the turning axis R of the optical element holding member 28, as illustrated in FIG. 2.

A turning angle around the turning axis R of the first prism 61 by the transmission wire 24 is less than 180 degrees.

The first prism 61 is fixed to a hole portion position of the optical element holding member 28 such that light of the shooting optical axis O reflected by the triangular prism 61b can pass through the first cylindrical section 65. Note that the first prism 61 is disposed such that a center of the objective lens 61a is positioned on the central axis X.

The support base 50 is provided with a trapezoidal prism 62 on the other surface, i.e., a surface on the opposite side along the central axis X of the plate-shaped extension section 50a. A second prism 63 is fixed to the second cylindrical section 66 in the support base 50. The second prism 63 is also disposed such that light of the shooting optical axis O can pass through the second cylindrical section 66.

Thus, the support base 50 is provided with the first prism 61, the trapezoidal prism 62, and the second prism 63, and light of the shooting optical axis O incident on the objective lens 61a in the first prism 61 is reflected by the triangular prism 61b in the first prism 61, the trapezoidal prism 62, and the second prism 63, and is image-formed on the image pickup device 22 via the image-forming lens 21.

A tension spring 35 has both its ends respectively connected to an inner surface of the exterior tube 11 and a bottom of the optical element holding member 28. The one end of the tension spring 35 is hooked on a spring stop pin (not illustrated) provided on an inner peripheral surface of the exterior tube 11, and the other end of the tension spring 35 is hooked on a spring stop pin (not illustrated) provided in the optical element holding member 28.

The tension spring 35 assumes a role of keeping tension of the transmission wire 24 constant by turning the optical element holding member 28 around the turning axis R by its extension and contraction.

The transmission wire 24 is set such that the longitudinal axis K and the turning axis P of the operation rod 8a are parallel to each other and the shooting optical axis O and the central axis X are parallel to each other, and a position of the operation rod 8a in such a state is set as a neutral position in the present embodiment.

At the neutral position in the present embodiment, the central axis X and the turning axis P are in an orthogonal relationship within a paper plane of FIG. 2, and the turning axis R and the turning axis Q are in a parallel relationship. Note that the central axis X and the turning axis P may be separated from each other in a direction perpendicular to the paper plane.

The endoscope 1 according to the present embodiment configured as described above can change a direction of a field of view in an upward, downward, leftward, or rightward direction by an inclination operation of the operation lever 8 provided in the operation section 3.

More specifically, as illustrated in FIG. 5, in the endoscope 1, when the operation lever 8 provided in the operation section 3 is operated to be inclined in a clockwise direction (a direction of arrow U in FIG. 5) around the turning axis Q from a neutral state, the longitudinal axis (K) of the operation rod 8a moves from Kn to Ku, and the transmission wire 24 that is connected to the shaft receiving section 8b and passes through the coil 32 is drawn toward the operation section 3 in a longitudinal direction of the insertion section 2.

On the other hand, when the operation lever 8 is operated to be inclined in a counterclockwise direction (a direction of arrow D in FIG. 5) around the turning axis Q from the neutral state, the longitudinal axis (K) of the operation rod 8a moves from Kn to Kd, the optical element holding member 28 turns in the clockwise direction around the turning axis R when the transmission wire 24 connected to the shaft receiving section 8b is loosened and the tension spring 35 attached to the distal end portion of the exterior tube 11 shrinks, and the transmission wire 24 that passes through the coil 32 is fed out toward the distal end of the insertion section 2 in the longitudinal direction of the insertion section 2.

The optical element holding member 28 connected to a distal end of the transmission wire 24 turns around the turning axis R as a first axis to match advance/retreat movement of the transmission wire 24. As a result, the first prism 61 as an optical element provided in the optical element holding member 28 turns around the turning axis R.

Accordingly, when the operation lever 8 is operated to be inclined in the U direction in FIG. 5 from the neutral state, the optical element holding member 28 is turned in a counterclockwise direction (a direction of arrow β) around the turning axis R, and the first prism 61 provided in the optical element holding member 28 is also turned in the counterclockwise direction (the direction of arrow β) around the turning axis R.

As a result, the shooting optical axis O of the endoscope 1 deflects in the counterclockwise direction (the direction of arrow β), and light having Ou as its axis in the drawing is propagated to be reflected by the first prism 61, the trapezoidal prism 62, and the second prism 63, and is image-formed on the image pickup device 22 via the image-forming lens 21 held in the image pickup system holding barrel 13.

In other words, in the endoscope 1, when the operation lever 8 provided in the operation section 3 is operated to be inclined in the clockwise direction (the direction of arrow U in FIG. 5) from the neutral state, the direction of a field of view is changed in an upward direction (the direction of arrow β).

On the other hand, when the operation lever 8 is operated to be inclined in the counterclockwise direction (the direction of arrow D) in FIG. 5 from the neutral state, the optical element holding member 28 is turned in a clockwise direction (a direction of arrow α) around the turning axis R, and the first prism 61 provided in the optical element holding member 28 is also turned in the clockwise direction (the direction of arrow α) around the turning axis R.

As a result, the shooting optical axis O of the endoscope 1 also deflects in the clockwise direction (the direction of arrow α), and light having Od as its axis in the drawing is image-formed on the image pickup device 22 by a similar function to the function described above.

In other words, in the endoscope 1, when the operation lever 8 provided in the operation section 3 is operated to be inclined in the counterclockwise direction (the direction of arrow D in FIG. 5) from the neutral state, the direction of a field of view is changed in a downward direction (the direction of arrow α).

Thus, the endoscope 1 can change the direction of a field of view in an upward or downward direction by an inclination operation in a back-and-forth direction of the operation lever 8 provided in the operation section 3.

Figure 6:
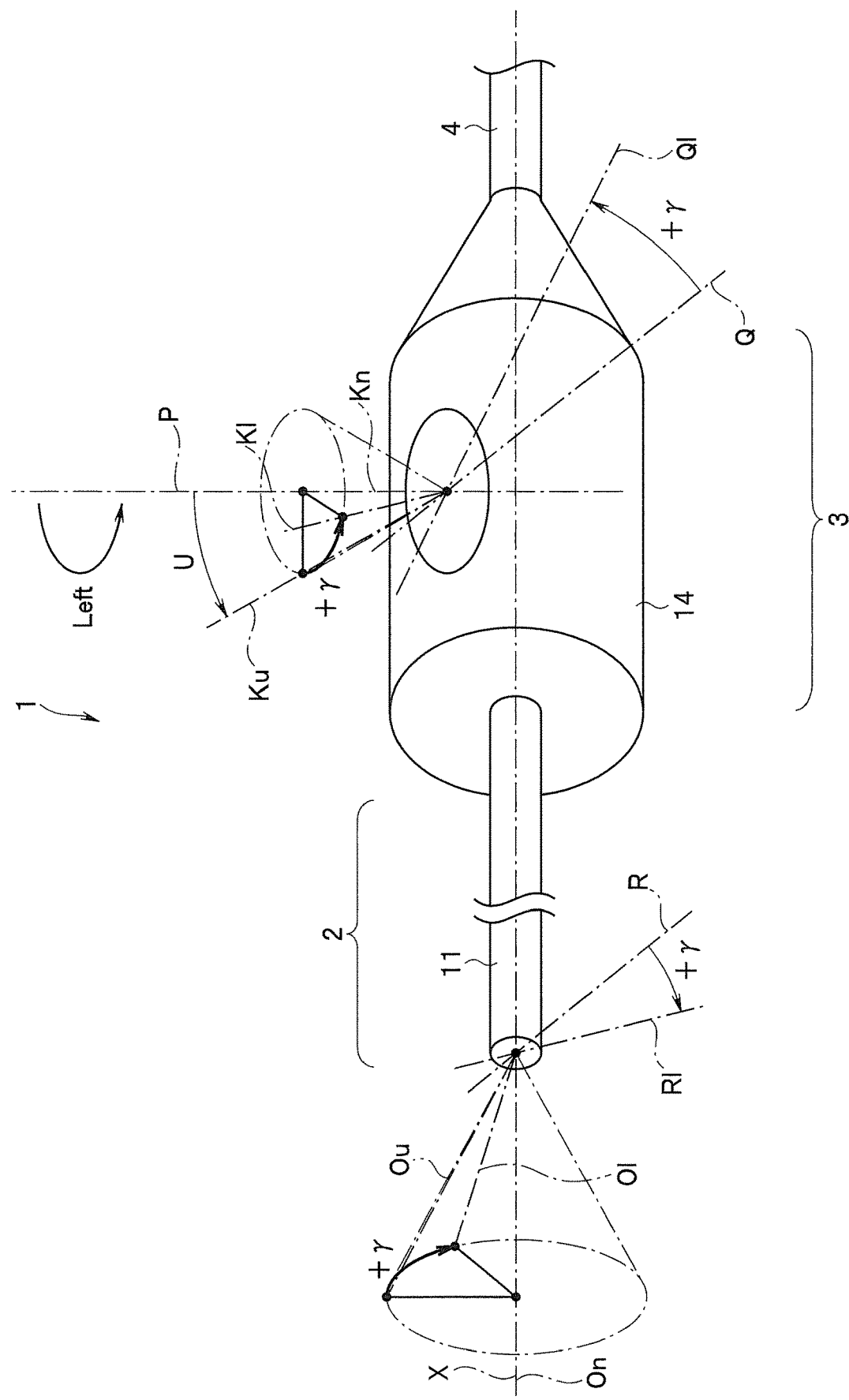
FIG. 6 is a diagram for describing an operation in a state where an operation lever is operated to be inclined leftward with the operation lever operated to be inclined forward according to the first embodiment.

As illustrated in FIG. 6, in the endoscope 1, when the operation lever 8 provided in the operation section 3 is operated to be inclined in a direction of arrow Left around the turning axis P from a state where the operation lever 8 is inclined in the direction of arrow U around the turning axis Q (a state where the longitudinal axis of the operation rod 8*a* is Ku) from a neutral position (a state where the longitudinal axis of the operation rod is Kn), a turning force around the turning axis P is applied to the cylindrical member 30 via the shaft 23 fixed to the shaft receiving section 8*b* in the operation lever 8, the cylindrical member 30 disposed within the operation section 3 turns around the turning axis P, and the longitudinal axis of the operation rod 8*a* moves to Kl with the turning. With a turning operation of the cylindrical member 30, the bevel gear 31*b* also turns around the turning axis P, and the bevel gear 31*a* that meshes with the bevel gear 31*b* also turns around the central axis X.

If the cylindrical member 30 has turned by an angle +γ (a direction of arrow) around the turning axis P, the bevel gear 31*b* and the bevel gear 31*a* mesh with each other at a turning transmission ratio of 1:1. Accordingly, the bevel gear 31*a* also turns by the angle +γ around the central axis X.

If the bevel gear 31*a* has turned by the angle +γ (the direction of arrow) around the central axis X, the exterior tube 11 to which the bevel gear 31*a* is fixed similarly turns by the angle +γ (the direction of arrow) around the central axis X, and the first prism 61, the trapezoidal prism 62, and the second prism 63, together with the optical element holding member 28 disposed inside, also turn by the angle +γ (the direction of arrow) around the central axis X.

As a result, the shooting optical axis Ou of the endoscope 1 also turns by the angle +γ (the direction of arrow) around the central axis X, and light having Ol as its axis in the drawing is image-formed on the image pickup device 22 by a similar function to the above-described function.

In other words, in the endoscope 1, when the operation lever 8 provided in the operation section 3 is further operated to be inclined leftward (in the direction of arrow Left) (the longitudinal axis of the operation rod 8*a* is Kl) in a state where the operation lever 8 is inclined forward (in the direction of arrow U) (the longitudinal axis of the operation rod 8*a* is Ku) from the neutral position (the longitudinal axis of the operation rod 8*a* is Kn), the direction of a field of view is changed in a leftward direction (from Ou to Ol), like an operation direction.

Figure 7:
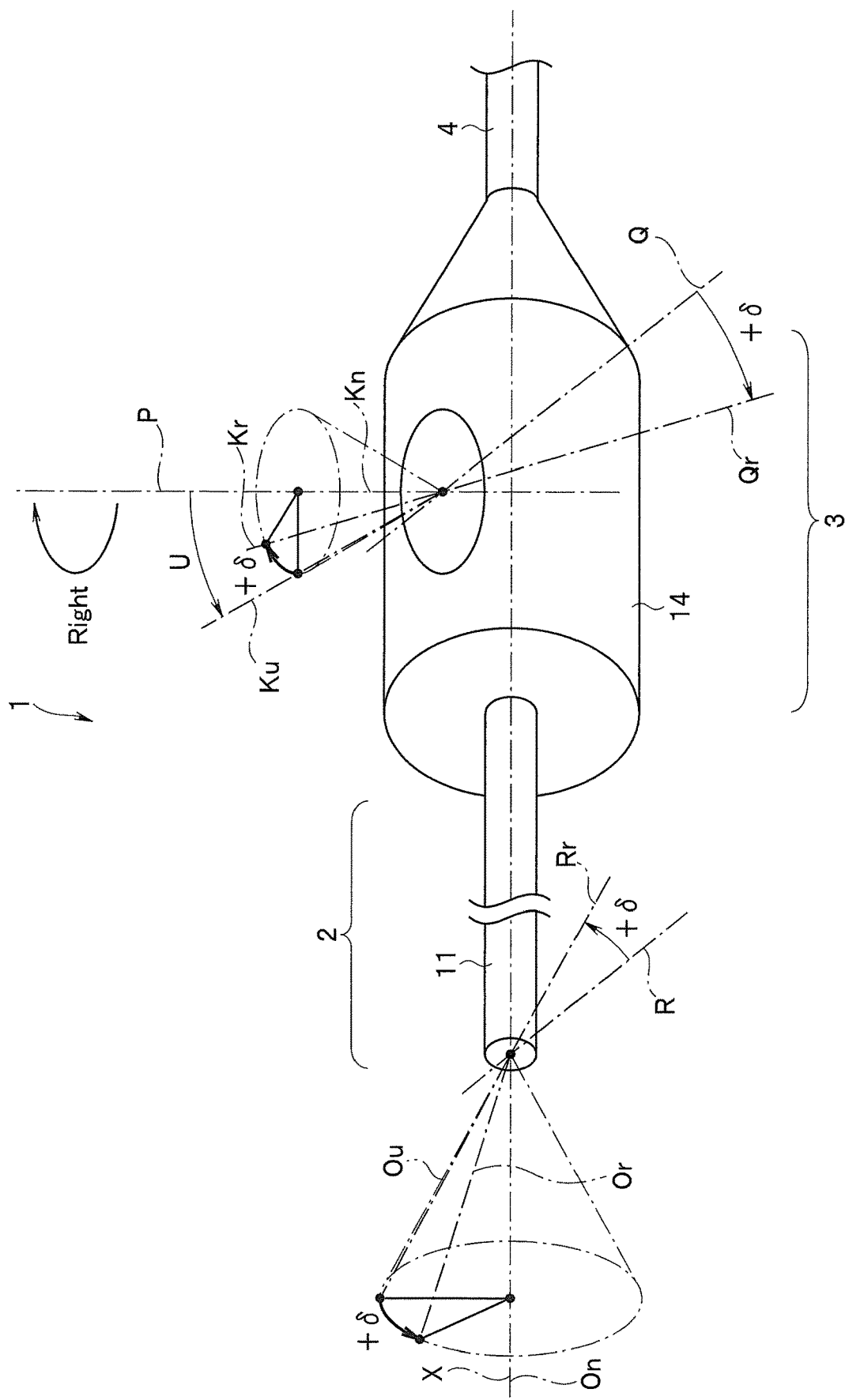
FIG. 7 is a diagram for describing an operation in a state where the operation lever is operated to be inclined rightward with the operation lever operated to be inclined forward according to the first embodiment.

As illustrated in FIG. 7, in the endoscope 1, when the operation lever 8 provided in the operation section 3 is operated to be inclined in a direction of arrow Right around the turning axis P from a state where the operation lever 8 is inclined in the direction of arrow U around the turning axis Q (the longitudinal direction of the operation rod is Ku) from the neutral position (the longitudinal axis of the operation rod is Kn), the direction of a field of view is changed in a rightward direction (from Ou to Or), like an operation direction, by a reverse function to the function in the above-described description of the direction of arrow Left (FIG. 6). Note that a turning direction and an angle of each of the sections with the operation of the operation lever 8 are denoted by δ in the drawing.

Figure 8:
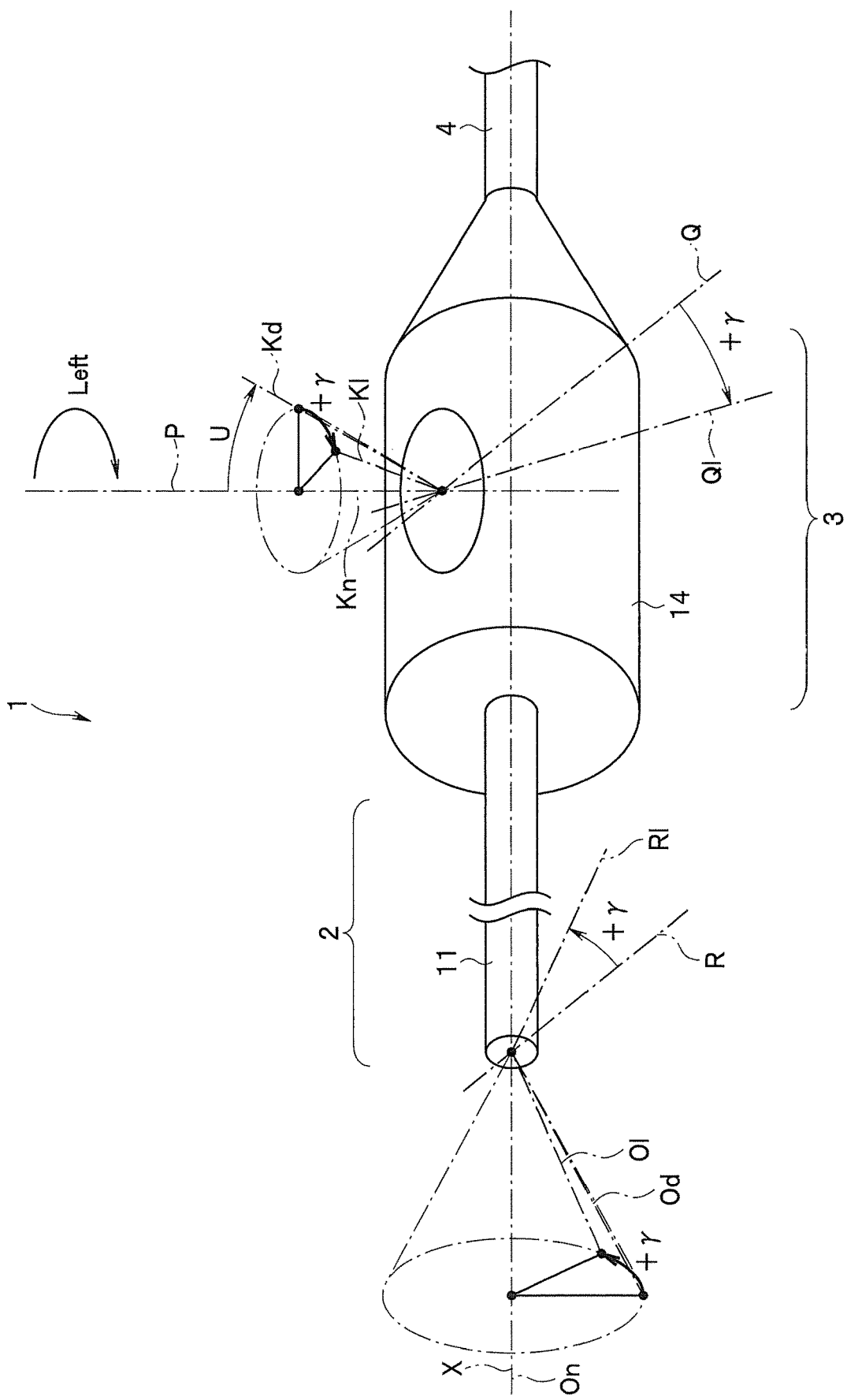
FIG. 8 is a diagram for describing an operation in a state where the operation lever is operated to be inclined leftward with the operation lever operated to be inclined backward according to the first embodiment.
Figure 9:
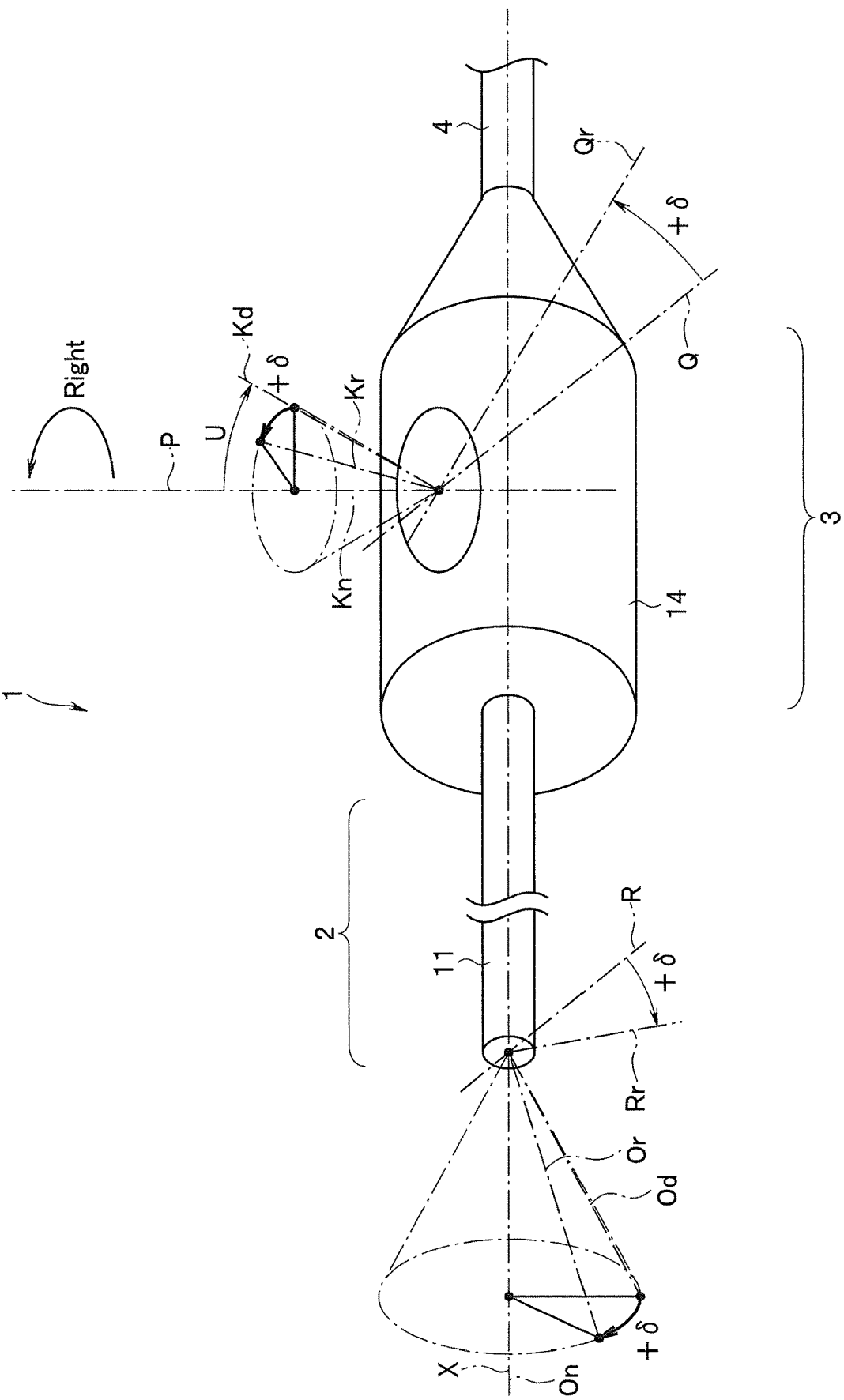
FIG. 9 is a diagram for describing an operation in a state where the operation lever is operated to be inclined rightward with the operation lever operated to be inclined backward according to the first embodiment.

Similarly, as illustrated in FIGS. 8 and 9, in the endoscope 1, when the operation lever 8 provided in the operation section 3 is operated to be inclined in the direction of arrow Left or the direction of arrow Right around the turning axis P from a state where the operation lever 8 is inclined in the direction of arrow D around the turning axis Q (the longitudinal direction of the operation rod 8*a* is Kd) from the neutral position (the longitudinal axis of the operation rod is Kn), the direction of a field of view is changed in a leftward or rightward direction (from Od to Ol or Or), like the operation direction, by a reverse function to the function illustrated in FIGS. 6 and 7. Note that a turning direction and an angle of each of the sections with the operation of the operation lever 8 are denoted by γ or δ in the drawing.

Thus, the endoscope 1 can change, by an inclination operation in a right-and-left direction of the operation lever 8 provided in the operation section 3, the direction of a field of view in the same right-and-left direction as the right-and-left direction of the operation lever 8.

As described above, the first prism 61 as an optical element is disposed turnably around the axis R perpendicular to the central axis X as a longitudinal axis and around an axis parallel to the central axis X in the distal end portion of the insertion section 2 so that the direction of a field of view can be changed in an upward, downward, leftward, or rightward direction.

The operation lever 8 as an operating member has the longitudinal axis K, and is disposed in the operation section 3. The operation lever 8 is turnable from the neutral position around the axis Q and the axis P that are perpendicular to each other. The cylindrical member 30 as a turning member has the axis P provided parallel to the longitudinal axis K at the neutral position of the operation lever 8, is disposed such that turning around the axis P of the operation lever 8 is transmitted, and turns around the axis P by inclining the operation lever 8.

The transmission wire 24 as a first transmitting member is connected to the optical element holding member 28 and the operation lever 8, and turning around the axis R is transmitted to the first prism 61 in response to an inclination operation around the axis Q of the operation lever 8.

Further, the gear section 31 as a second transmitting member includes the bevel gears 31*a* and 31*b*, and turns in response to turning about the axis P of the operation lever 8. The bevel gear 31*a* in the proximal end portion is connected to the cylindrical member 30, and turning around the axis X is transmitted to the first prism 61 in response to a turning operation around the axis P of the operation lever 8 with the operation lever 8 turned around the axis Q from the neutral position.

Therefore, in the endoscope 1 according to the present embodiment, the operation lever 8 as one operating member provided in the operation section 3 can move the direction of a field of view upward, downward, leftward, or rightward in the same direction as an inclination direction of the operation lever 8 when an optical axis deflects in an upward, downward, leftward, or rightward direction by inclining and turning the first prism 61 provided at the distal end of the insertion section 2.

In the endoscope 1 according to the present embodiment, even when the shooting optical axis O deflects in an upward or downward direction from the central axis X by an operation in a UD direction of the operation lever, a field of view movement operation can be intuitively performed over a wide field of view change range without inversion of field of view movement direction when the operation lever is inclined in a leftward or rightward direction.

As a result, the endoscope 1 is configured such that its field of view can be easily varied over a wide range by one operating member for an intended direction and site while a user such as a doctor sees an operative site image by the image display section 6 as a monitor during an operation, to improve operability at the time of changing the field of view.

As described above, the first and second transmitting members and the first, second, third, and fourth axes respectively correspond to the transmission wire 24, the bevel gears 31*a* and 31*b*, the turning axis R, the central axis X, the turning axis Q, and the turning axis P in the first embodiment.

Modification to First Embodiment

Figure 10:
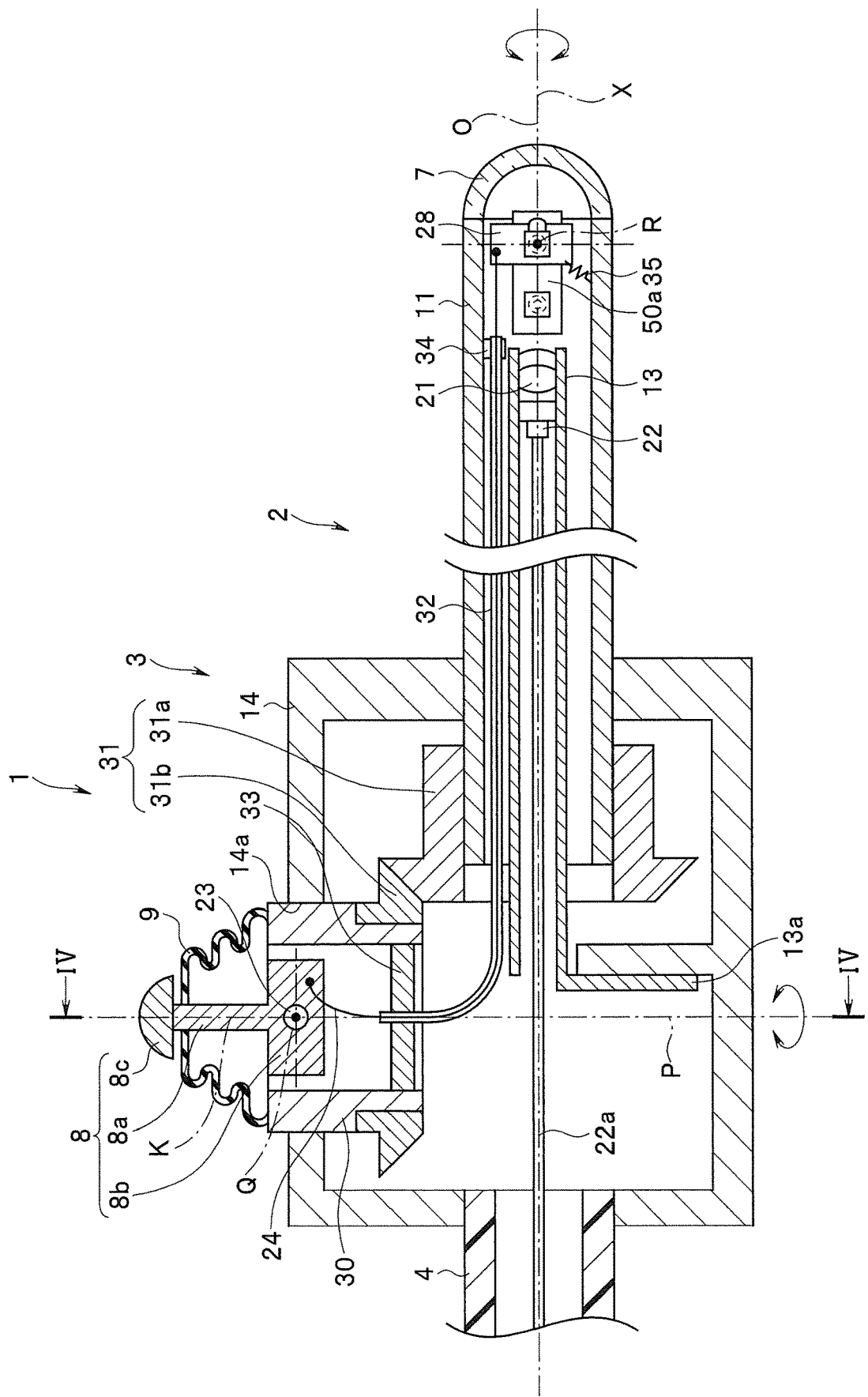
FIG. 10 is a cross-sectional view illustrating a configuration of an endoscope according to a modification to the first embodiment.

FIG. 10 is a cross-sectional view illustrating a configuration of an endoscope according to a modification to the first embodiment, and FIGS. 11 to 14 are diagrams for describing a function of the endoscope according to the modification to the first embodiment. More specifically, a transmission wire 24 is fixed to a portion on the side of an exterior tube 11 in a shaft receiving section 8b (the right side of a turning axis P in FIG. 10).

Even an endoscope 1 thus configured can also change a direction of a field of view in an upward or downward direction by performing an inclination operation in a back-and-forth direction from a state of an initial position of the operation lever 8.

However, in the endoscope 1, when the operation lever 8 is operated to be inclined forward (in a direction of arrow U in FIG. 5), the transmission wire 24 is fed out forward so that the direction of a field of view is changed in a downward direction (DOWN), unlike in the foregoing.

On the other hand, when the operation lever 8 is operated to be inclined backward (in a direction of arrow D in FIG. 5), the transmission wire 24 is drawn backward so that the direction of a field of view is changed in an upward direction (UP).

Similarly, for a field of view in a right-and-left direction, the direction of a field of view is changed in a direction opposite to an inclination direction of the operation lever 8, as illustrated in FIGS. 11 to 14.

Figure 11:
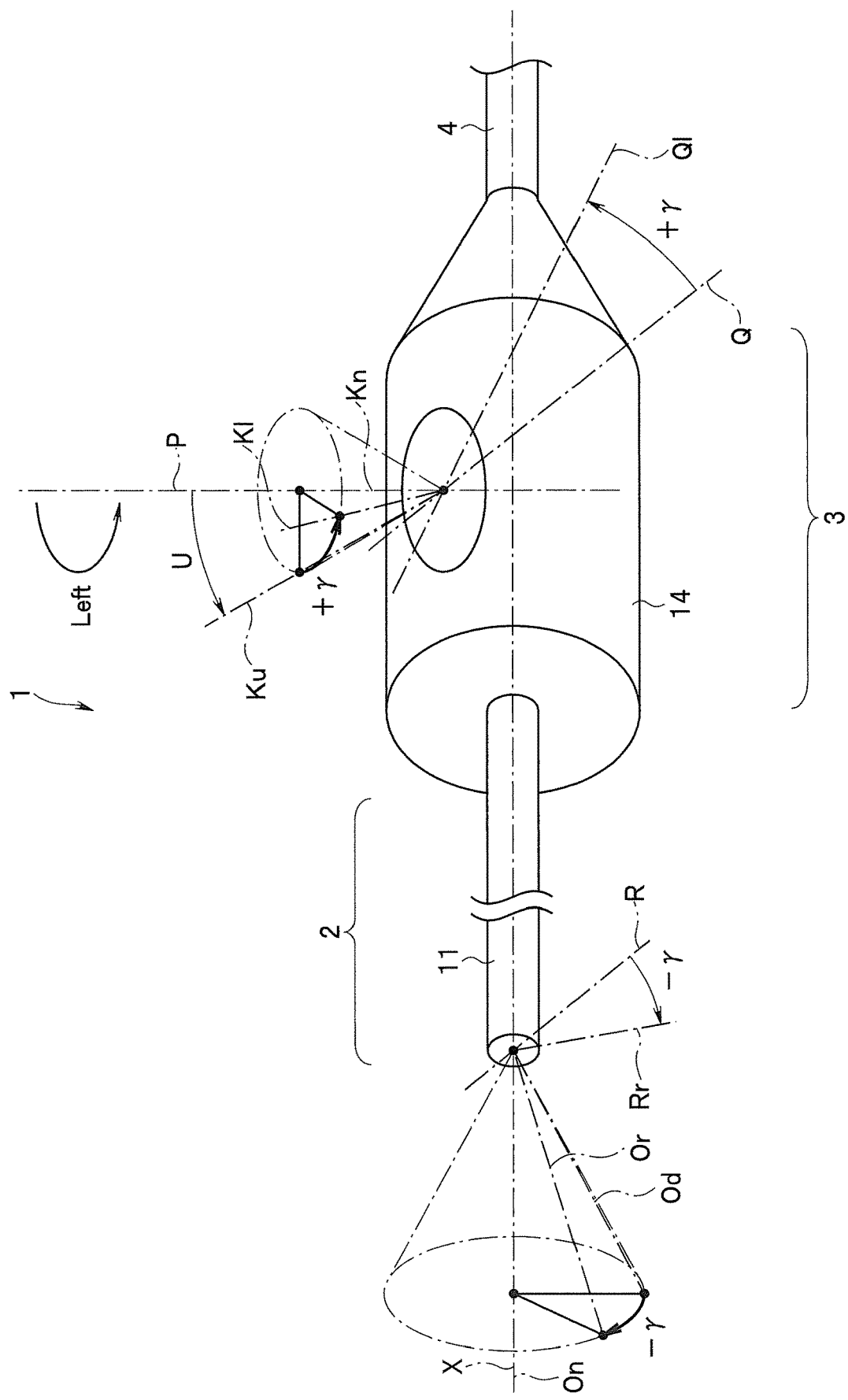
FIG. 11 is a diagram for describing an operation in a state where an operation lever is operated to be inclined leftward with the operation lever operated to be inclined forward according to the modification to the first embodiment.

FIG. 11 shows that in the endoscope 1, the direction of a field of view when the operation lever 8 provided in an operation section 3 is operated to be inclined in a direction of arrow Left around the turning axis P from a state where the operation lever 8 is inclined in the direction of arrow U around a turning axis Q (a state where a longitudinal axis of an operation rod 8a is Ku) from a neutral position (a state where the longitudinal axis of the operation rod is Kn) is changed in a rightward direction (from Od to Or).

Figure 12:
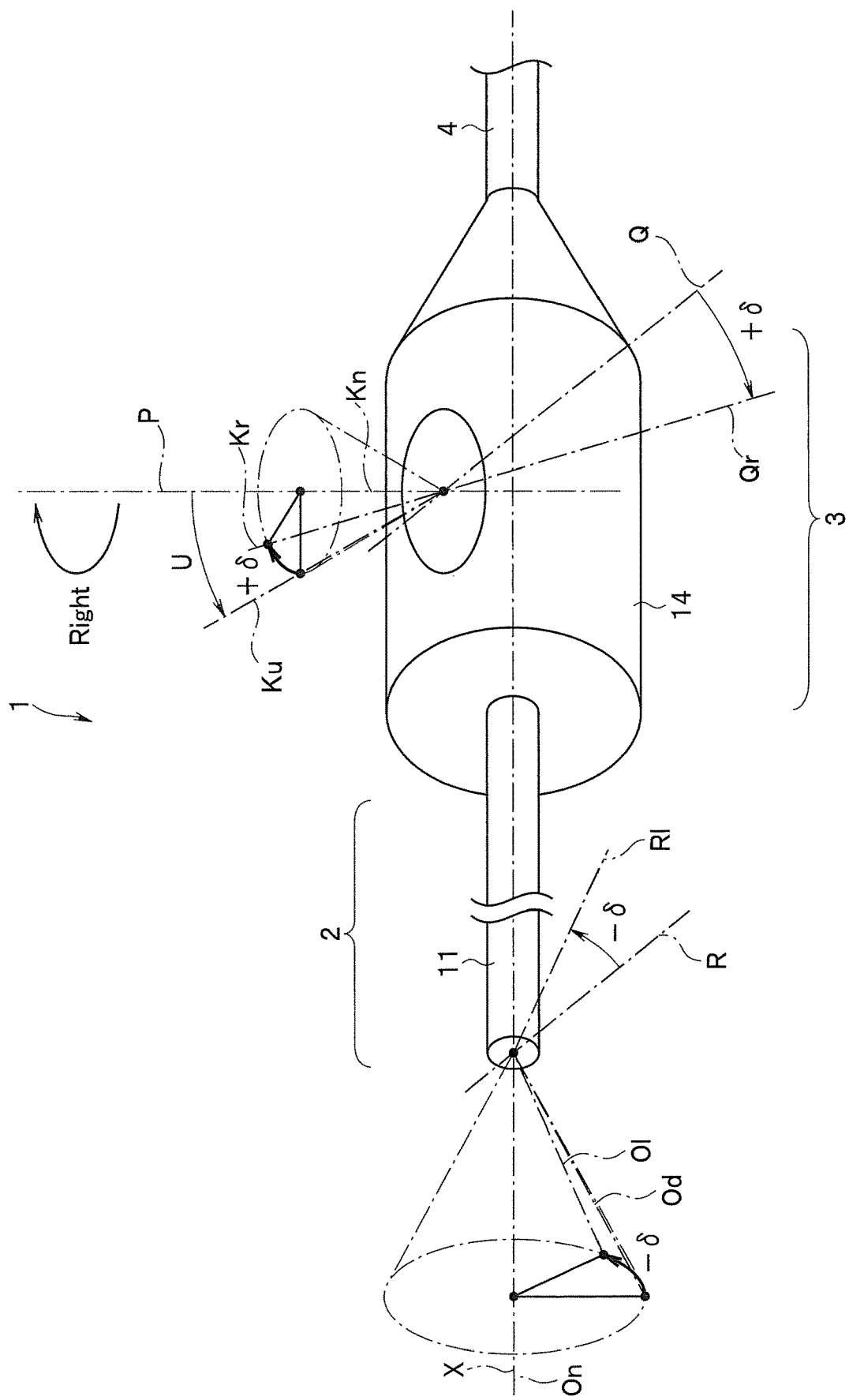
FIG. 12 is a diagram for describing an operation in a state where the operation lever is operated to be inclined rightward with the operation lever operated to be inclined forward according to the modification to the first embodiment.

FIG. 12 shows that in the endoscope 1, the direction of a field of view when the operation lever 8 provided in the operation section 3 is operated to be inclined in a direction of arrow Right around the turning axis P from a state where the operation lever 8 is inclined in the direction of arrow U around the turning axis Q (the longitudinal axis of the operation rod is Ku) from the neutral position (the longitudinal axis of the operation rod is Kn) is changed in a leftward direction (from Od to Ol).

Figure 13:
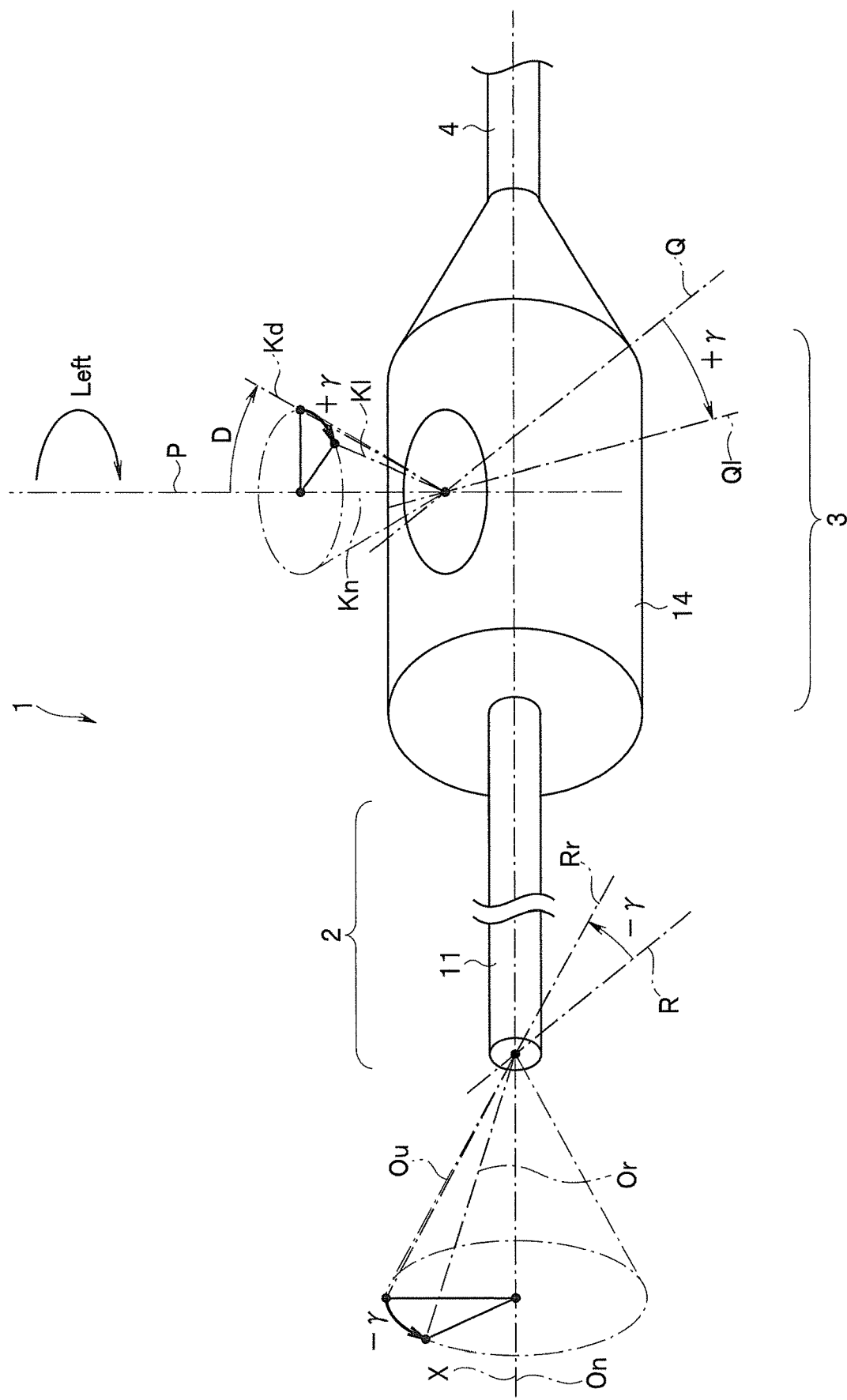
FIG. 13 is a diagram for describing an operation in a state where the operation lever is operated to be inclined leftward with the operation lever operated to be inclined backward according to the modification to the first embodiment.
Figure 14:
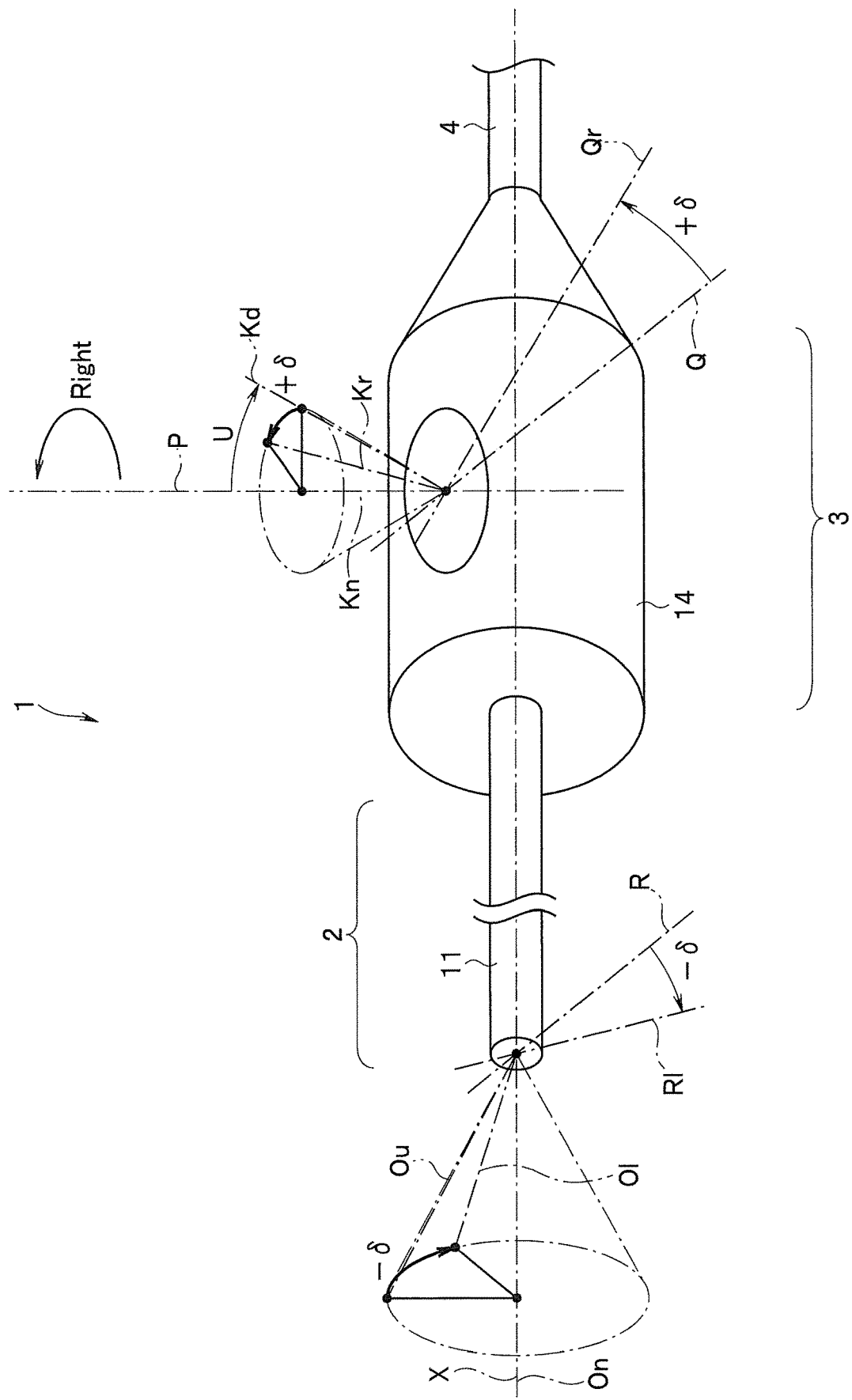
FIG. 14 is a diagram for describing an operation in a state where the operation lever is operated to be inclined rightward with the operation lever operated to be inclined backward according to the modification to the first embodiment.

Similarly, as illustrated in FIGS. 13 and 14, in the endoscope 1, when the operation lever 8 provided in the operation section 3 is operated to be inclined in the direction of arrow Left or the direction of arrow Right around the turning axis P from a state where the operation lever 8 is inclined in the direction of arrow D around the turning axis Q (the longitudinal axis of the operation rod 8a is Kd) from the neutral position (the longitudinal axis of the operation rod is Kn), the direction of a field of view is changed in a leftward or rightward direction (from Ou to Or or Ol), like an operation direction, by a reverse function to function illustrated in FIGS. 11 and 12.

In other words, in the present modification, the operation direction and a field of view change direction are in a relationship inverted in an up-and-down or right-and-left direction (rotated by 180 degrees) by a reverse function to the function illustrated in FIGS. 5 to 9. Therefore, the endoscope 1 according to the present embodiment can correspond to the operation direction of the operation lever 8 that suits a user's preference by changing a fixing position of the transmission wire 24.

Second Embodiment

Then, an endoscope according to a second embodiment of the present invention will be described below with reference to the drawings. Note that in the following description, the same components as the components described in the above-described first embodiment are assigned the same reference numerals, and detailed description of the components is omitted.

Figure 15:
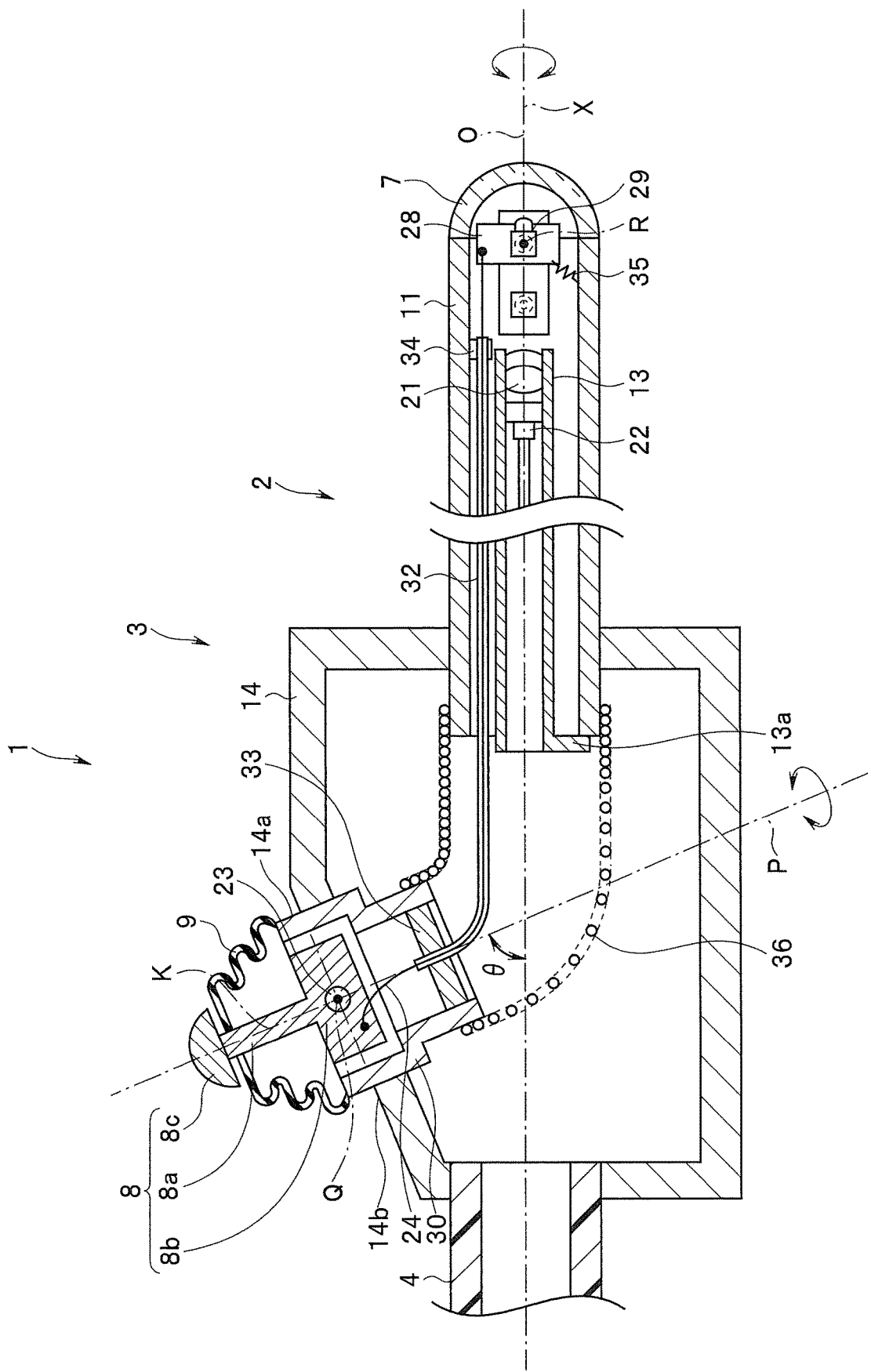
FIG. 15 is a cross-sectional view for describing a configuration of an endoscope according to a second embodiment.
Figure 16:
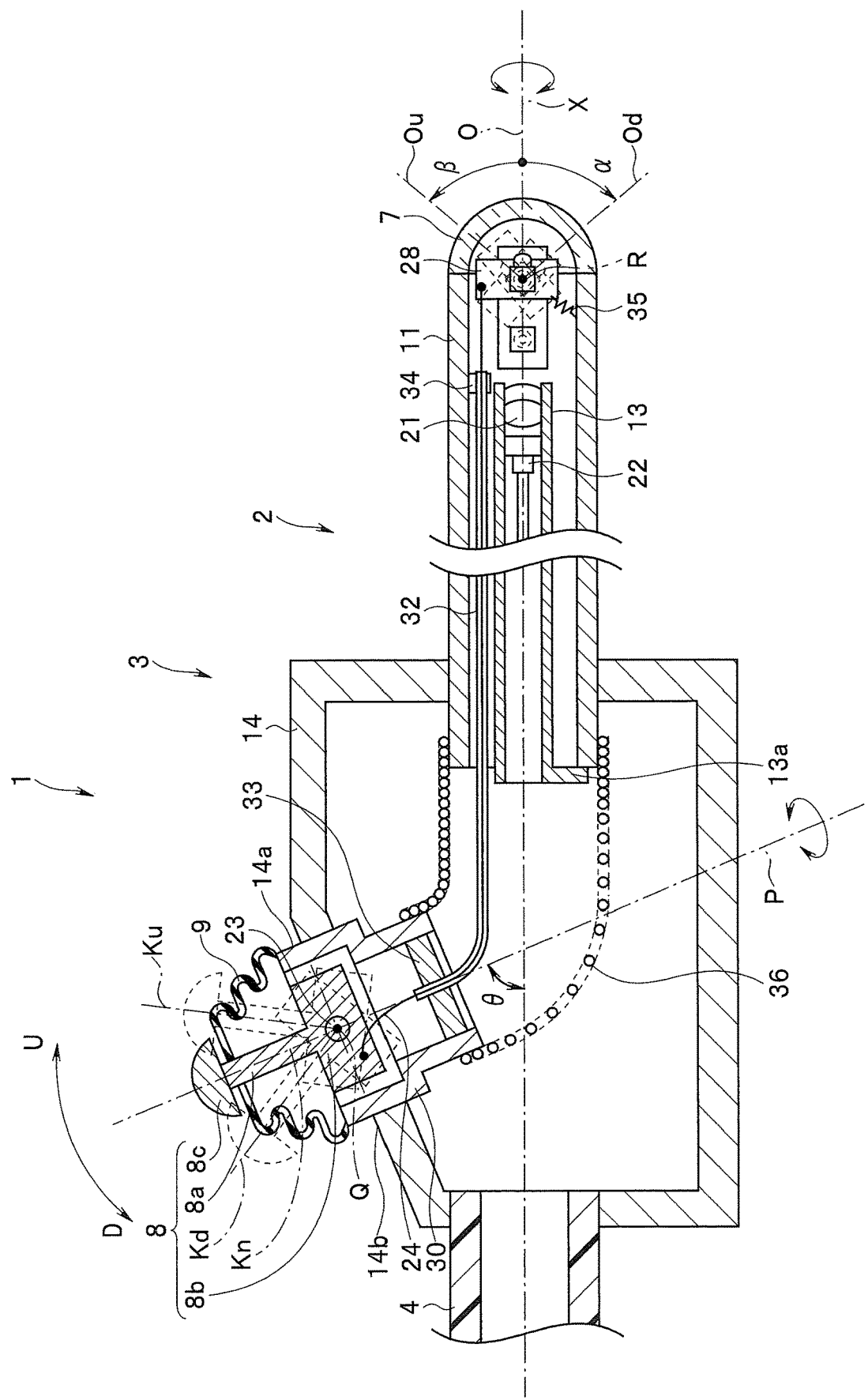
FIG. 16 is a cross-sectional view for describing an operation of the endoscope according to the second embodiment.

FIG. 15 is a cross-sectional view for describing a configuration of the endoscope according to the second embodiment, and FIG. 16 is a cross-sectional view for describing an operation of the endoscope according to the second embodiment.

An endoscope 1 according to the present embodiment differs from the endoscope 1 according to the first embodiment in a configuration in which turning around a turning axis P of a cylindrical member 30 provided in an operation section 3 configured to change an angle θ formed between the turning axis P and a central axis X and a direction of a field of view is transmitted to an exterior tube 11 in an insertion section 2, as illustrated in FIG. 15.

More specifically, a planar section 14b partially inclined is formed in an upper part of a cylindrical operation section frame body 14, and the cylindrical member 30 is connected turnably around the turning axis P, like in the first embodiment, to the planar section 14b. The turning axis P crosses the central axis X in a state inclined by the angle θ.

In other words, the central axis X and an axis obtained by projecting the turning axis P on a plane parallel to the turning axis P and including the central axis X cross each other at a predetermined angle θ.

The predetermined angle θ can be optionally set in a range of 0 degrees to 90 degrees by changing a formation direction of an opening section 14a with respect to the planar section 14b.

Note that the central axis X and the turning axis P may be separated from each other in a direction perpendicular to a paper plane.

Further, both ends of a flexible shaft 36 are integrally fixed with adhesive or the like to an end portion of the cylindrical member 30 and a proximal end portion of the exterior tube 11. The flexible shaft 36 has flexibility by a structure in which a wire rod composed of a metal or the like is wound in a coil shape, and transmits without delay turning of two turning bodies generally having an eccentricity or/and a deflection angle. As a result, movement obtained when the cylindrical member 30 turns around the turning axis P is transmitted to the exterior tube 11 via the flexible shaft 36.

At a neutral position in the present embodiment, a longitudinal axis K of an operation rod 8a and the turning axis P are parallel to each other, and a shooting optical axis O and the central axis X are parallel to each other, and further a turning axis R and a turning axis Q are in a parallel relationship, like in the first embodiment.

As the flexible shaft 36 is used, a fixing plate section 13a is fixed to the exterior tube 11 with a screw, not illustrated.

In the endoscope 1 configured as described above, when an operation lever 8 provided in the operation section 3 is operated to be inclined in a clockwise direction (a direction of arrow U in the drawing) around the turning axis Q from a neutral state, the direction of a field of view is changed in an upward direction (UP) by a similar function to the function in the first embodiment, as illustrated in FIG. 16. When the operation lever 8 is operated to be inclined in a counterclockwise direction (a direction of arrow D in the drawing) from the neutral state, the direction of a field of view is changed in a downward direction (DOWN).

Thus, the endoscope 1 can change the direction of a field of view in an upward or downward direction by an inclination operation in a back-and-forth direction of the operation lever 8 provided in the operation section 3.

A relationship between an operation of the operation lever 8 and a change in the direction of a field of view (i.e., a deflection of the shooting optical axis) described in FIGS. 6 to 9 in the first embodiment is also the same as a relationship in the present embodiment, and thus description is omitted. Only turning transmission between the cylindrical member 30 and the exterior tube 11 specific to the present embodiment will be described. As illustrated in FIG. 6, for example, in the endoscope 1, when the operation lever 8 in the operation section 3 is operated to be inclined by an angle γ in a Left direction around the turning axis P from a state where the operation lever 8 is inclined in the U direction around the turning axis Q (the longitudinal axis of the operation rod 8a is Ku) from a neutral position (the longitudinal axis of the operation rod is Kn), a turning force is applied to the cylindrical member 30 via a shaft 23 fixed to a shaft receiving section 8b in the operation lever 8 so that the cylindrical member 30 disposed within the operation section 3 turns by the angle γ around the turning axis P, and the longitudinal axis of the operation rod 8a moves to Kl with the turning. The flexible shaft 36 also turns with a turning operation of the cylindrical member 30, and the exterior tube 11 also turns by the angle γ around the central axis X with the turning.

Although a relationship between the central axis X and the turning axis P is limited to an orthogonal relationship on the paper plane of FIG. 2 in the first embodiment, the angle θ formed between the central axis X and the turning axis P can be freely set by using the flexible shaft 36 as a second transmitting member.

As a result, there can be provided an endoscope having better operability because an angle of the operation lever 8 to the operation section can be preferably set to match an application of the endoscope. Note that the flexible shaft can also be replaced with a mechanical joint.

As described above, the operation lever 8 can move the direction of a field of view upward, downward, leftward, or rightward in the same direction as an inclination direction of the operation lever 8, like in the first embodiment.

As described above, the first and second transmitting members and the first, second, third, and fourth axes respectively correspond to a transmission wire 24, the flexible shaft 36, the turning axis R, the central axis X, the turning axis Q, and the turning axis P in the second embodiment.

Further, components to which various types of modifications described in the first embodiment can be applied in the endoscope 1 according to the present embodiment can also be deformed to the components.

Third Embodiment

An endoscope according to a third embodiment of the present invention will be described below with reference to the drawings. Note that in the following description, the same components as the components described in the above-described first and second embodiments are assigned the same reference numerals, and detailed description of the components is omitted.

Figure 17:
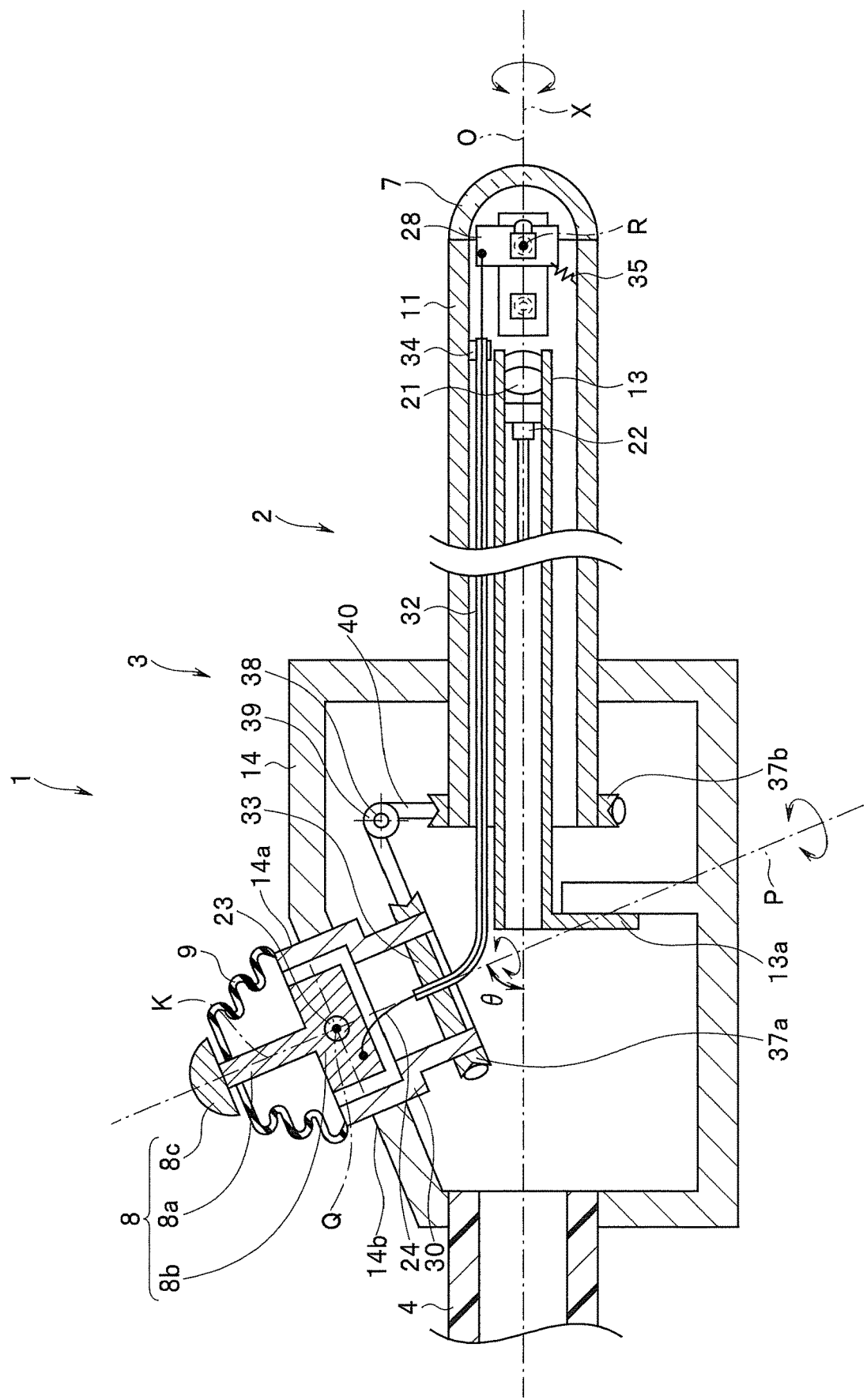
FIG. 17 is a cross-sectional view for describing a configuration of an endoscope according to a third embodiment.
Figure 18:
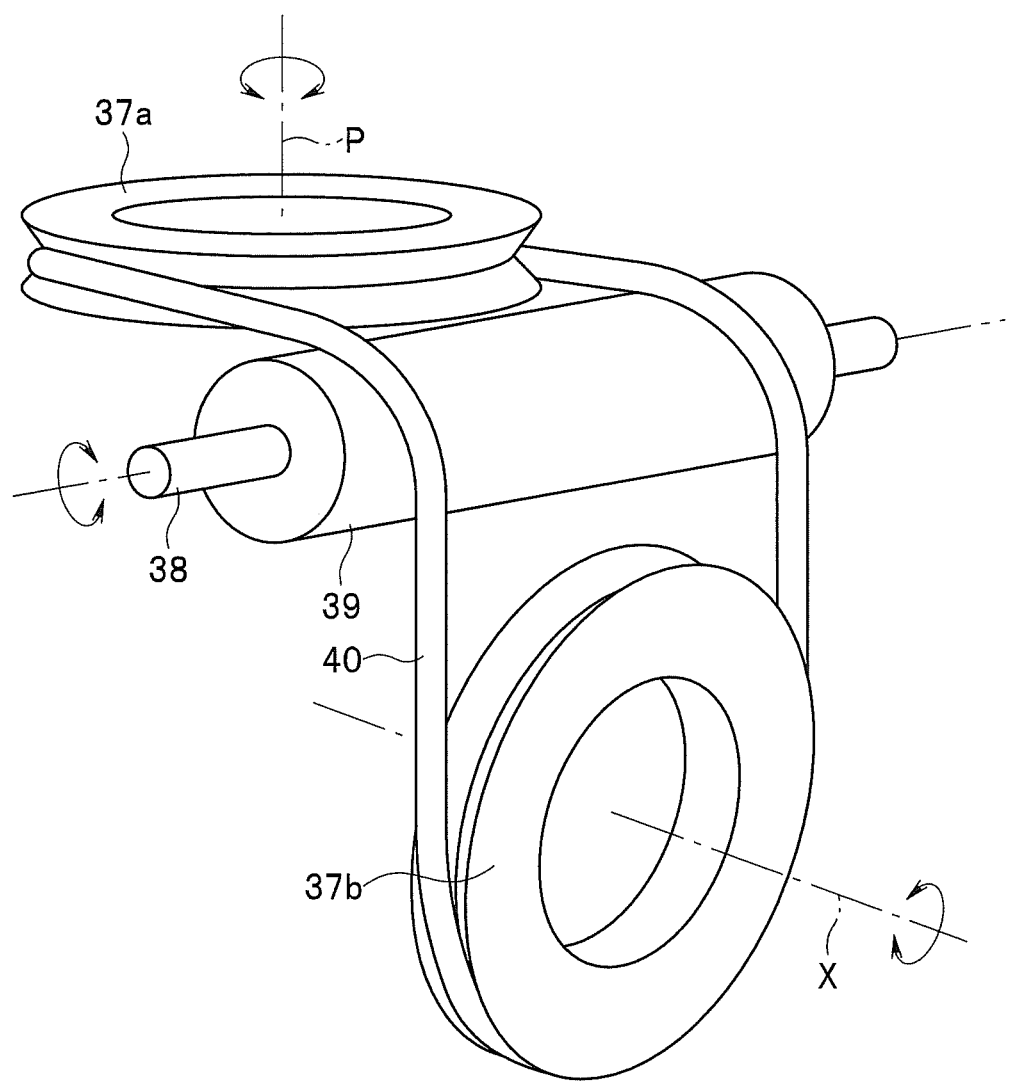
FIG. 18 is a diagram for describing a transmitting member in the endoscope according to the third embodiment.
Figure 19:
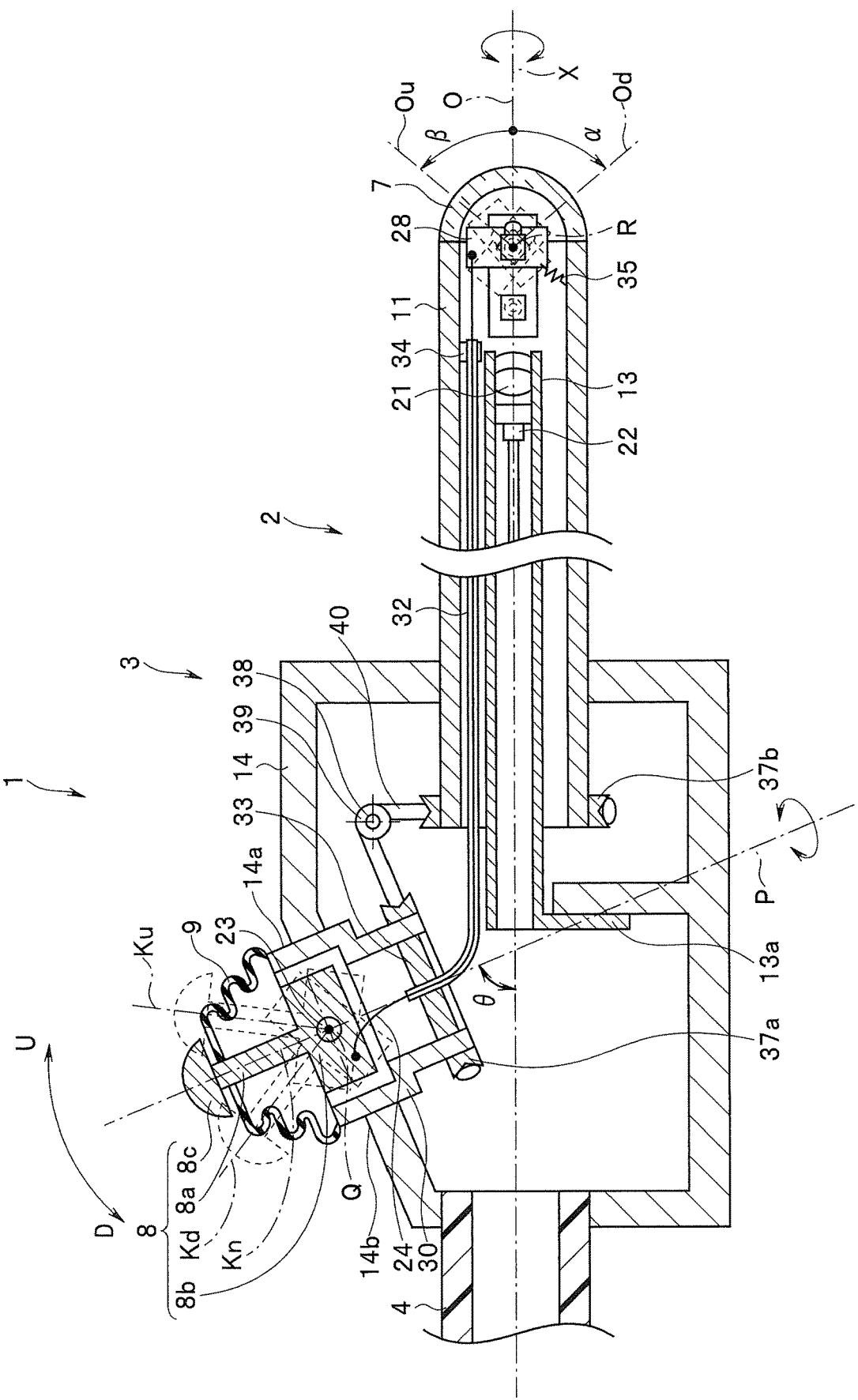
FIG. 19 is a cross-sectional view for describing an operation of the endoscope according to the third embodiment.

FIG. 17 is a cross-sectional view for describing a configuration of an endoscope according to the third embodiment, FIG. 18 is a diagram for describing a transmitting member in the endoscope according to the third embodiment, FIG. 19 is a cross-sectional view for describing an operation of the endoscope according to the third embodiment, and FIGS. 20 to 23 are diagrams for describing a function of the endoscope according to the third embodiment. Note that an angle θ formed between a central axis X and a turning axis P is indicated by 90 degrees for simplicity in FIGS. 20 to 23.

An endoscope 1 according to the present embodiment differs from the endoscopes 1 according to the first and second embodiments in a configuration in which turning around the turning axis P of a cylindrical member 30 provided in an operation section 3 configured to change a direction of a field of view is transmitted to an exterior tube 11 in an insertion section 2, as illustrated in FIG. 17.

More specifically, a pulley 37a is fixed coaxially with the turning axis P to an end portion of the cylindrical member 30, and a pulley 37b is fixed coaxially with the central axis X to a proximal end portion of the exterior tube 11. Respective outer diameters of the pulleys 37a and 37b are the same, V-shaped or U-shaped grooves are respectively formed on outer peripheries of the pulleys 37a and 37b, and a belt 40, described below, is stretched between the grooves.

A relay shaft 38 is fixed in a direction perpendicular to a paper plane of FIG. 17 inside an operation section frame body 14, and a roller 39 is turnably connected to the relay shaft 38. The belt 40 is stretched among the pulleys 37a and 37b and the roller 39 without loosening nor sliding in a form as illustrated in FIG. 18. The roller 39 has an outer peripheral surface on which the belt 40 easily slides.

In other words, the belt 40 assumes a role of converting a direction of a turning operation around the turning axis P of the pulley 37a via the roller 39 and transmitting the turning operation to turning around the central axis X of the pulley 37b.

Although a relationship between the central axis X and the turning axis P is limited to an orthogonal relationship on the paper plane of FIG. 2 in the first embodiment, by using the pulleys 37a and 37b, the roller 39, and the belt 40 as a second transmitting member, the belt 40 can freely change its curvature angle so that the angle θ formed between the central axis X and the turning axis P can be freely set.

At a neutral position in the present embodiment, a longitudinal axis K of an operation rod 8a and the turning axis P are coaxial with and parallel to each other, a shooting optical axis O and the central axis X are coaxial with and parallel to each other, and further a turning axis R and a turning axis Q are in a parallel relationship, like in the first and second embodiments.

In the endoscope 1 configured as described above, when an operation lever 8 provided in the operation section 3 is operated to be inclined in a clockwise direction (a direction of arrow U in FIG. 19) around the turning axis Q from a neutral state, a longitudinal axis Kn of the operation rod 8a moves to Ku, and a transmission wire 24 that is connected to a shaft receiving section 8b and passes through a coil 32 is drawn toward the operation section 3 in a longitudinal direction of the insertion section 2.

On the other hand, when the operation lever 8 is operated to be inclined in a counterclockwise direction (a direction of arrow D in FIG. 19) around the turning axis Q from the neutral state, the longitudinal axis Kn of the operation rod 8a moves to Kd, an optical element holding member 28 turns in the clockwise direction around the turning axis R when the transmission wire 24 connected to the shaft receiving section 8b is loosened and a tension spring 35 attached to a distal end portion of the exterior tube 11 shrinks, and the transmission wire 24 that passes through the coil 32 is fed out toward a distal end of the insertion section 2 in the longitudinal direction of the insertion section 2.

The optical element holding member 28 connected to a distal end of the transmission wire 24 turns around the turning axis R to match advance/retreat movement of the transmission wire 24. As a result, a first prism 61 as an optical element provided in the optical element holding member 28 turns around the turning axis R.

Accordingly, when the operation lever 8 is operated to be inclined in the direction of arrow U in FIG. 19 from the neutral state, the optical element holding member 28 turns in a counterclockwise direction (a direction of arrow β) around the turning axis R, and a trapezoidal prism 62 provided in the optical element holding member 28 also turns in the counterclockwise direction (the direction of arrow β) around the turning axis R.

As a result, the shooting optical axis O of the endoscope 1 deflects in the counterclockwise direction (the direction of arrow β), and light having Ou as its axis in the drawing is propagated to be reflected by the first prism 61, the trapezoidal prism 62, and a second prism 63, and is image-formed on an image pickup device 22 via an image-forming lens 21 held in an image pickup system holding barrel 13.

In other words, in the endoscope 1, when the operation lever 8 provided in the operation section 3 is operated to be inclined in the clockwise direction (the direction of arrow U in FIG. 19) from the neutral state, the direction of a field of view is changed in an upward direction (the direction of arrow β).

On the other hand, when the operation lever 8 is operated to be inclined in the direction of arrow D in FIG. 19 from the neutral state, the optical element holding member 28 turns in a clockwise direction (a direction of arrow α) around the turning axis R, and the first prism 61 provided in the optical element holding member 28 also turns in the clockwise direction (the direction of arrow α) around the turning axis R.

As a result, the shooting optical axis O of the endoscope 1 deflects in the clockwise direction (the direction of arrow α), and light having Od as its axis in the drawing is image-formed on the image pickup device 22 by a similar function to the above-described function.

In other words, in the endoscope 1, when the operation lever 8 provided in the operation section 3 is operated to be inclined in the counterclockwise direction (the direction of arrow D in FIG. 19) from the neutral state, the direction of a field of view is changed in a downward direction (the direction of arrow α).

Thus, the endoscope 1 can change the direction of a field of view in an upward or downward direction by an inclination operation in a back-and-forth direction of the operation lever 8 provided in the operation section 3.

Figure 20:
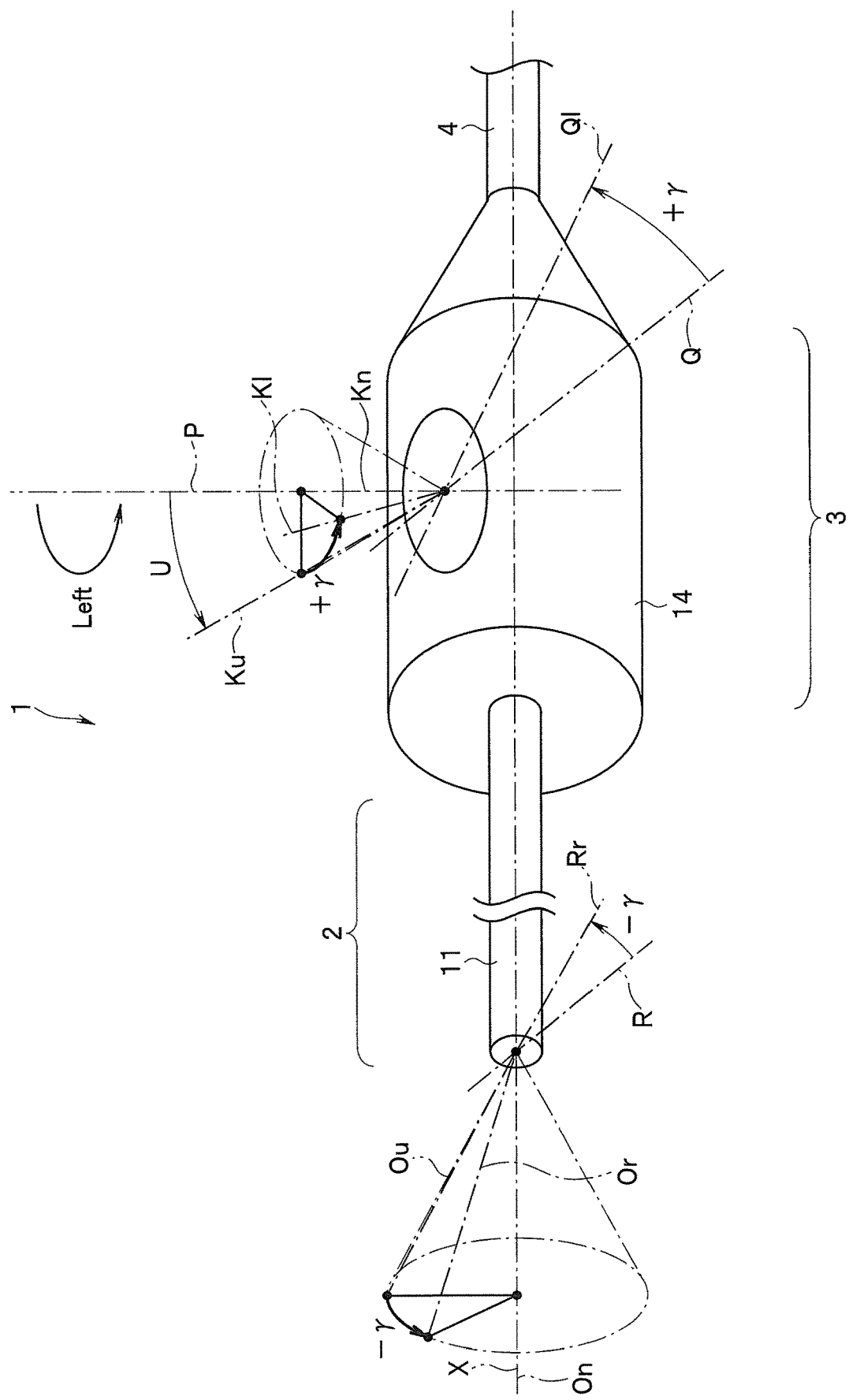
FIG. 20 is a diagram for describing an operation in a state where an operation lever is operated to be inclined leftward with the operation lever operated to be inclined forward according to the third embodiment.

As illustrated in FIG. 20, in the endoscope 1, when the operation lever 8 provided in the operation section 3 is operated to be inclined in a direction of arrow Left around the turning axis P from a state where the operation lever 8 is inclined in the direction of arrow U around the turning axis Q (the longitudinal axis of the operation rod 8a is Ku) from a neutral position (the longitudinal axis of the operation rod is Kn), a turning force is applied to the cylindrical member 30 via a shaft 23 fixed to the shaft receiving section 8b in the operation lever 8, the cylindrical member 30 disposed within the operation section 3 turns around the turning axis P, and the longitudinal axis of the operation rod 8a moves to Kl with the turning. The pulley 37a also turns with a turning operation of the cylindrical member 30, and the pulley 37b turns by a transmission function of the belt 40. The exterior tube 11 also turns around the central axis X with the turning of the pulley 37b.

When the cylindrical member 30 turns by an angle +γ (a direction of arrow) around the turning axis P, the pulley 37b turns around the central axis X by the same turning angle −γ (a direction of arrow) because the pulley 37b is the same in outer diameter as the pulley 37a. Therefore, the exterior tube 11 also similarly turns by the angle −γ (the direction of arrow) around the central axis X.

If the exterior tube 11 turns by the angle −γ (the direction of arrow) around the central axis X, the first prism 61, the trapezoidal prism 62, and the second prism 63, together with the optical element holding member 28 disposed inside, also turn by the angle −γ (the direction of arrow) around the central axis X.

In the endoscope 1, light of a shooting optical axis Or in a direction inclined rightward by a predetermined angle γ from light of a shooting optical axis Ou is incident on the trapezoidal prism 62, and the light is image-formed by the image pickup device 22 via the image-forming lens 21 held in the image pickup system holding barrel 13.

As a result, a shooting optical axis Od of the endoscope 1 also turns by the angle −γ around the central axis X, and light having Or as its axis in the drawing is image-formed on the image pickup device 22 by a similar function to the above-described function.

Note that plus and minus signs (+ and −) of the angle γ described in FIG. 20 are respectively assigned to the direction described in FIG. 6 in the first embodiment and a direction opposite to the direction.

In other words, in the endoscope 1, when the operation lever 8 provided in the operation section 3 is further operated to be inclined leftward (in the direction of arrow Left) (the longitudinal axis of the operation rod 8a is Kl) from a state where the operation lever 8 is inclined forward (the longitudinal axis of the operation rod 8a is Ku) from the neutral position (the longitudinal axis of the operation rod 8a is Kn), the direction of a field of view is changed in a rightward direction (from Ou to Or) opposite to an operation direction.

Figure 21:
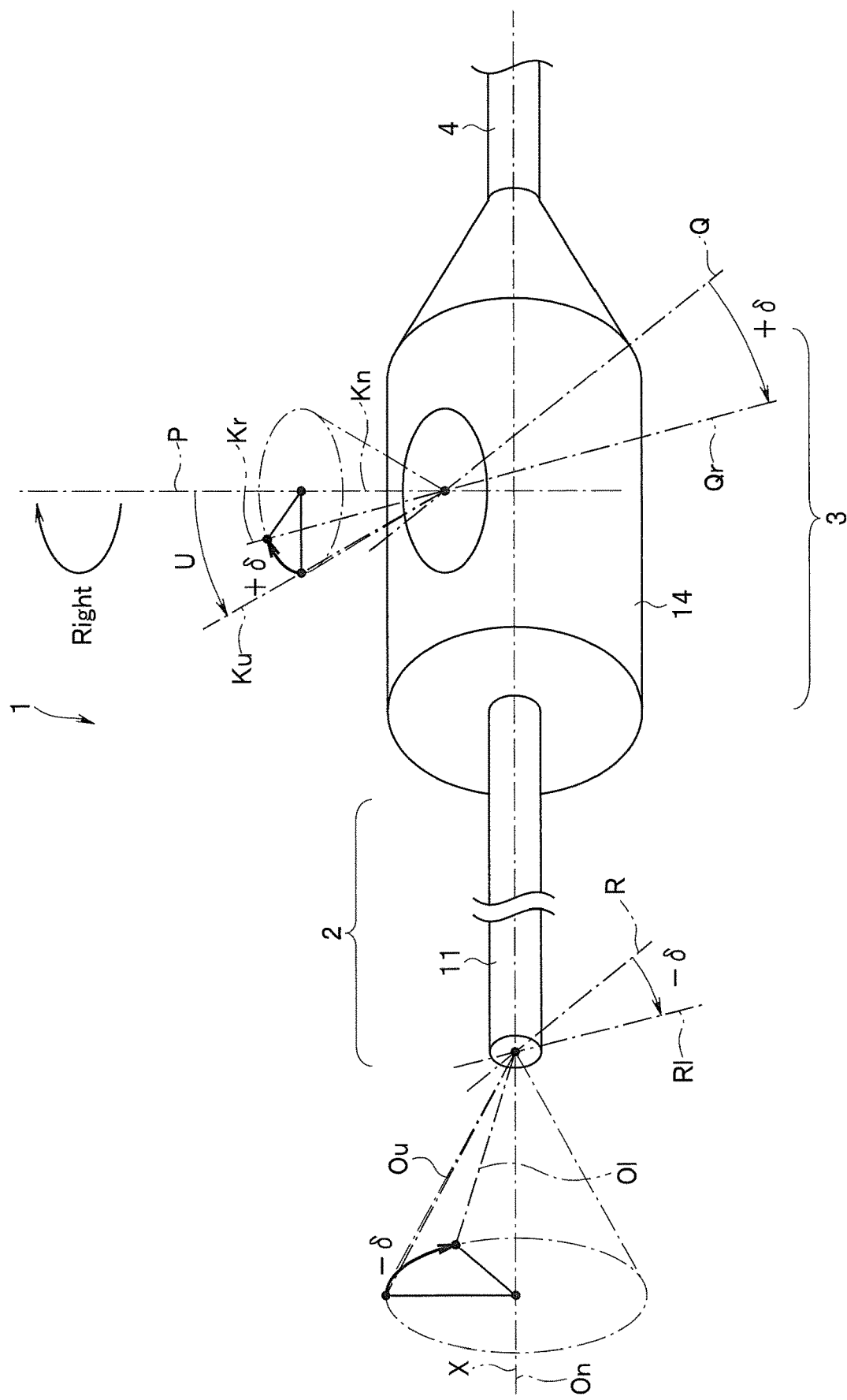
FIG. 21 is a diagram for describing an operation in a state where the operation lever is operated to be inclined rightward with the operation lever operated to be inclined forward according to the third embodiment.

As illustrated in FIG. 21, in the endoscope 1, when the operation lever 8 provided in the operation section 3 is operated to be inclined in a direction of arrow Right around the turning axis P from a state where the operation lever 8 is inclined in the direction of arrow U around the turning axis Q (the longitudinal axis of the operation rod is Ku) from the neutral position (the longitudinal axis of the operation rod is Kn), the direction of a field of view is changed in a leftward direction (from Od to Ol) opposite to the operation direction by a reverse function to the function in the above description of the Left direction (FIG. 20). Note that a turning direction and an angle of each of the sections with the operation of the operation lever are denoted by δ in the drawing, and plus and minus signs (+ and −) of the angle δ are respectively assigned to the direction described in FIG. 7 in the first embodiment and a direction opposite to the direction.

Figure 22:
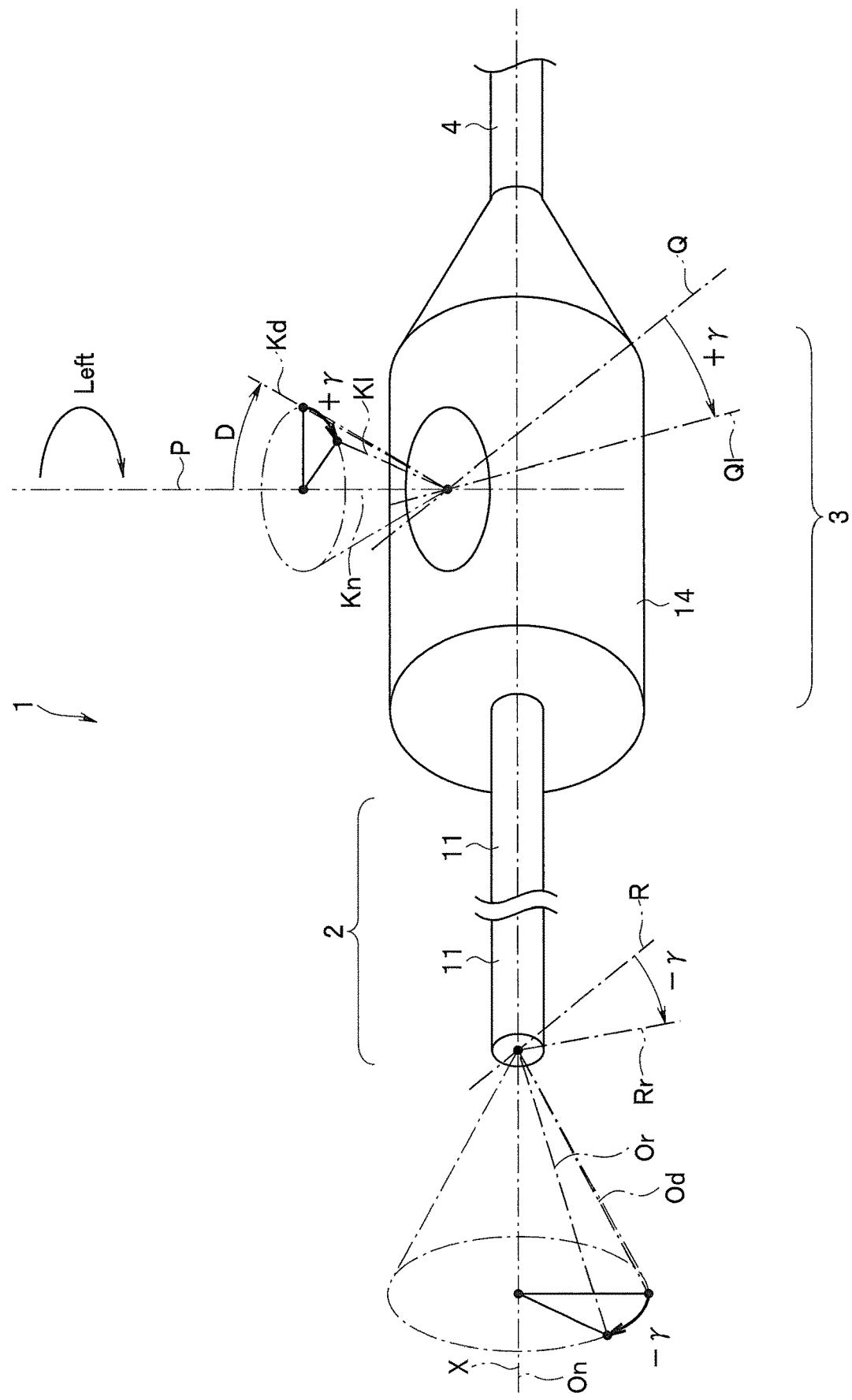
FIG. 22 is a diagram for describing an operation in a state where the operation lever is operated to be inclined leftward with the operation lever operated to be inclined backward according to the third embodiment.
Figure 23:
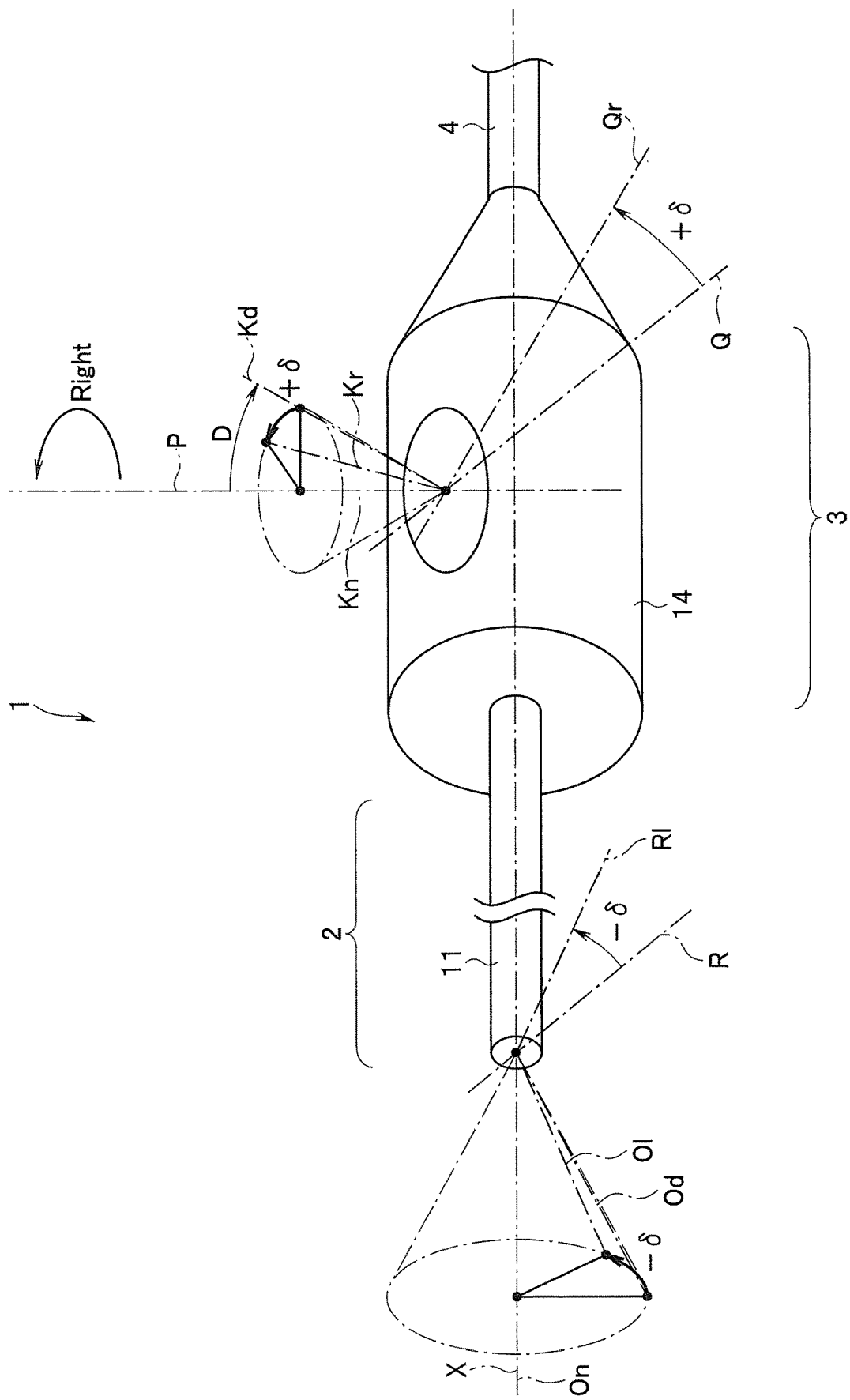
FIG. 23 is a diagram for describing an operation in a state where the operation lever is operated to be inclined rightward with the operation lever operated to be inclined backward according to the third embodiment.

Similarly, as illustrated in FIGS. 22 and 23, in the endoscope 1, when the operation lever 8 provided in the operation section 3 is operated to be inclined in the Left or Right direction around the turning axis P from a state where the operation lever 8 is inclined in the D direction around the turning axis Q (the longitudinal axis of the operation rod 8a is Kd) from the neutral position (the longitudinal axis of the operation rod is Kn), the direction of a field of view is changed in a rightward or leftward direction (from Ou to Or or Ol) opposite to the operation direction by a reverse function to the function illustrated in FIGS. 20 and 21.

Note that a turning direction and an angle of each of the sections with the operation of the operation lever are denoted by γ or δ in the drawing, and plus and minus signs (+ and −) are respectively assigned to the direction described in FIGS. 8 and 9 in the first embodiment and a direction opposite to the direction.

Thus, the endoscope 1 can change, by an inclination operation in a right-and-left direction of the operation lever 8 provided in the operation section 3, the direction of a field of view in a direction opposite to the right-and-left direction of the operation lever 8.

Therefore, the endoscope 1 according to the present embodiment can also change the direction of a field of view in an upward, downward, leftward, or rightward direction by an inclination operation in a back-and-forth or right-and-left direction of the operation lever 8 provided in the operation section 3, like in the first embodiment.

Note that the endoscope 1 is in a relationship in which the direction of a field of view is changed in an upward direction by a forward inclination operation, the direction of a field of view is changed in a downward direction by a backward inclination operation, the direction of a field of view is changed in a rightward direction by a leftward inclination operation, and the direction of a field of view is changed in a leftward direction by a rightward inclination operation in the operation direction of the operation lever 8, and is in a relationship of an imprint (inverted by 180 degrees) only in a right-and-left direction with the relationships in the first and second embodiments.

Accordingly, the endoscope 1 according to the present embodiment has an effect described in the first embodiment, and can correspond to an operation direction of the operation lever 8 that suits a user's preference to invert an operation direction and a direction of a field of view only leftward or rightward, unlike in the first embodiment.

The angle θ formed between the central axis X and the turning axis P can be freely set, like in the second embodiment, by using the pulleys 37a and 37b, the roller 39, and the belt 40. As a result, there can be provided an endoscope having better operability because an angle of the operation lever to the operation section can be preferably set to match an application of the endoscope.

As described above, the first and second transmitting members and the first, second, third, and fourth axes respectively correspond to the transmission wire 24, the belt 40 (and the pulleys 37a and 37b and the roller 39), the turning axis R, the central axis X, the turning axis Q, and the turning axis P in the third embodiment.

Modification to Third Embodiment

Figure 24:
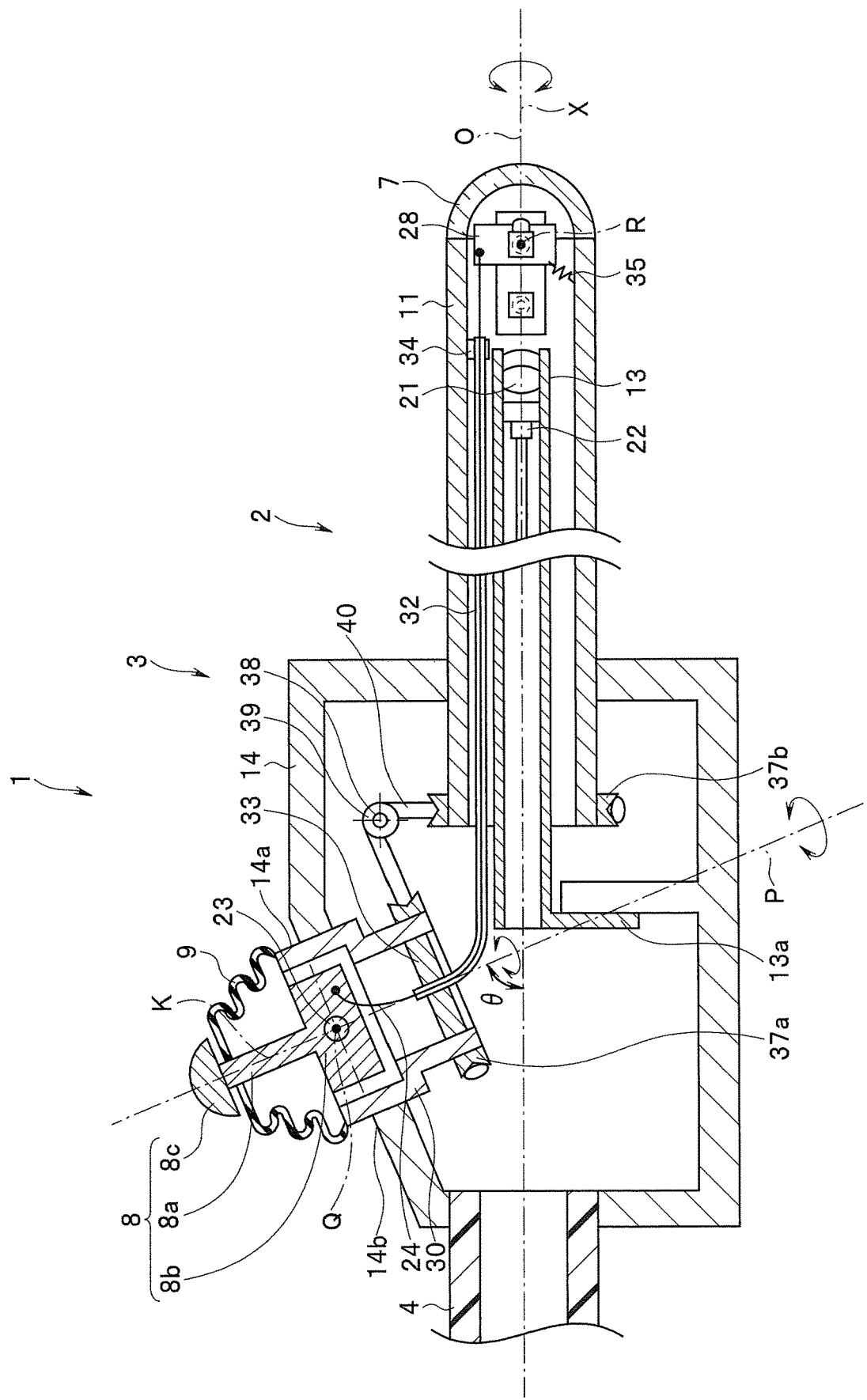
FIG. 24 is a perspective view illustrating a configuration of an endoscope according to a modification to the third embodiment.

FIG. 24 is a cross-sectional view illustrating a configuration of an endoscope according to a modification to the third embodiment, and FIGS. 25 to 28 are diagrams for describing a function of the endoscope according to the modification to the third embodiment. More specifically, a transmission wire 24 is fixed to a portion on the side of an exterior tube 11 in a shaft receiving section 8b (the right side of a turning axis P in FIG. 24), like in the modification to the first embodiment.

Even an endoscope 1 thus configured can change a direction of a field of view in an upward or downward direction by performing an inclination operation in a back-and-forth direction from a state of an initial position of the operation lever 8.

However, in the endoscope 1, when the operation lever 8 is operated to be inclined forward (in a direction of arrow U in FIG. 19), the transmission wire 24 is fed out forward so that the direction of a field of view is changed in a downward direction (DOWN), unlike in the foregoing.

Similarly, when the operation lever 8 is operated to be inclined backward (in a direction of arrow D in FIG. 19), the transmission wire 24 is drawn backward so that the direction of a field of view is changed in an upward direction (UP).

On the other hand, for a field of view in a right-and-left direction, the direction of a field of view is changed in the same direction as an inclination direction of the operation lever 8, as illustrated in FIGS. 25 to 28.

Figure 25:
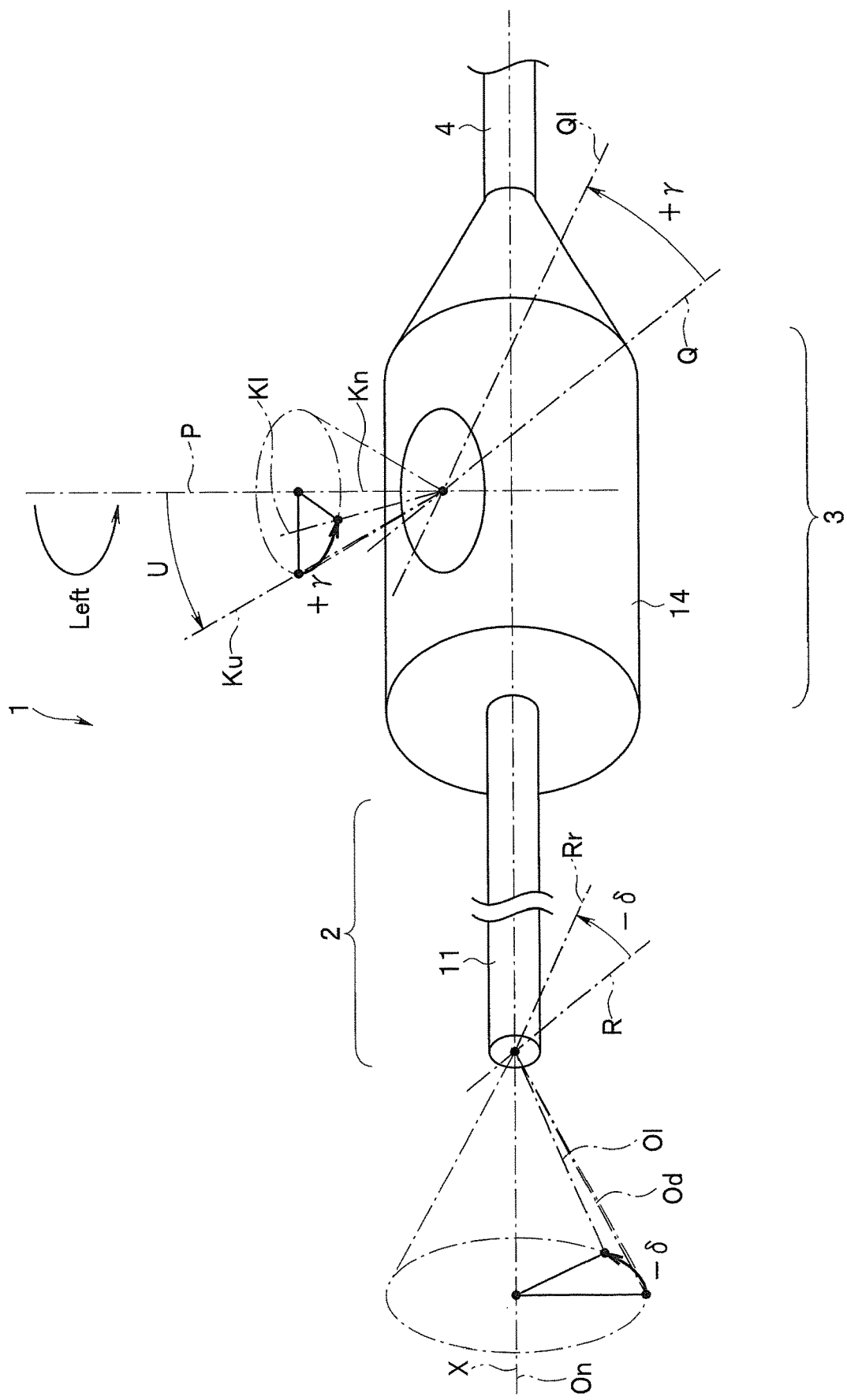
FIG. 25 is a diagram for describing an operation in a state where an operation lever is operated to be inclined leftward with the operation lever operated to be inclined forward according to the modification to the third embodiment.

FIG. 25 shows that in the endoscope 1, the direction of a field of view when the operation lever 8 provided in an operation section 3 is operated to be inclined in a direction of arrow Left around the turning axis P from a state where the operation lever 8 is inclined in the direction of arrow U around a turning axis Q (a state where a longitudinal axis of an operation rod 8a is Ku) from a neutral state (a state where the longitudinal axis of the operation rod is Kn) is changed in a rightward direction (from Od to Ol).

Figure 26:
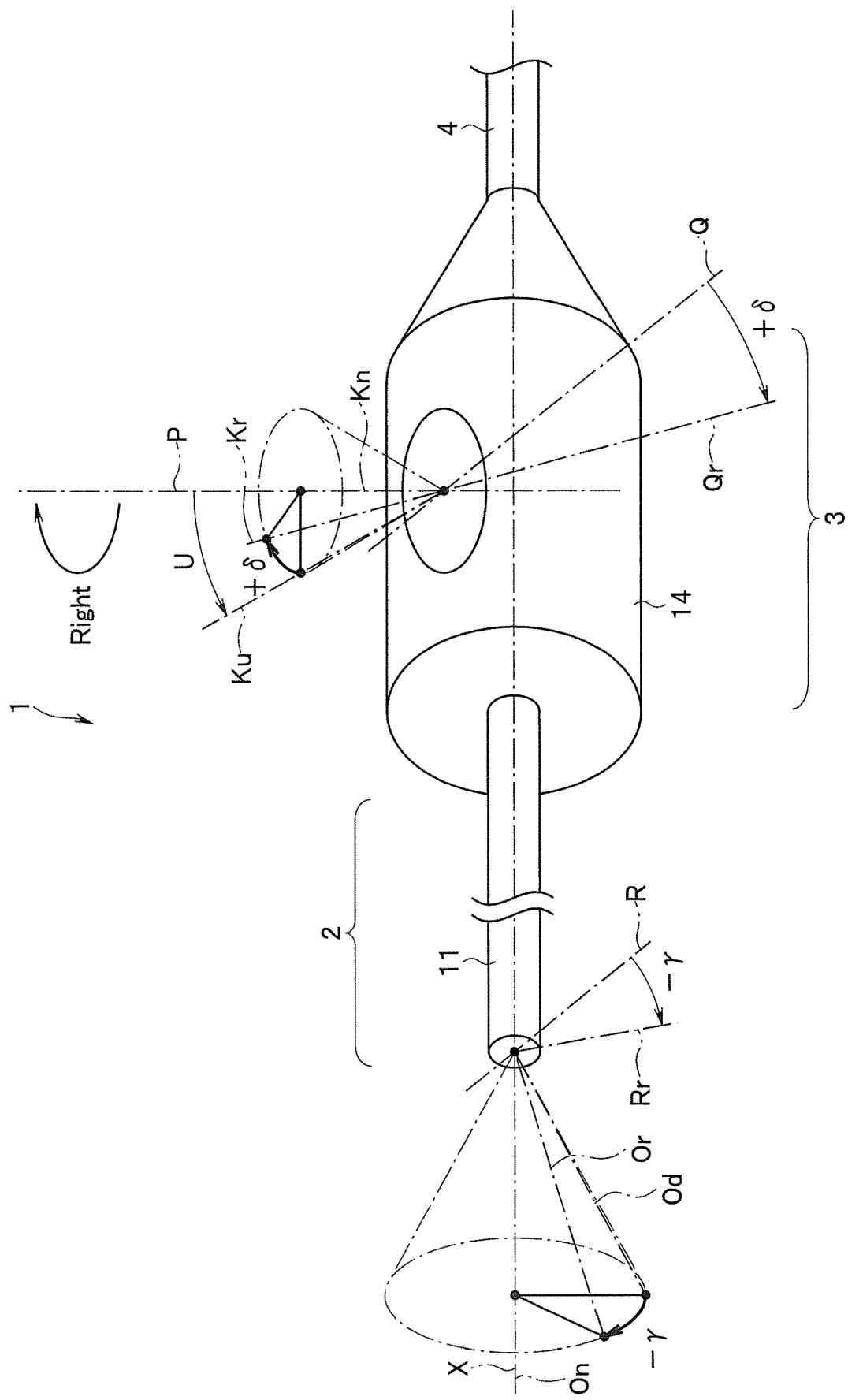
FIG. 26 is a diagram for describing an operation in a state where the operation lever is operated to be inclined rightward with the operation lever operated to be inclined forward according to the modification to the third embodiment.

FIG. 26 shows that in the endoscope 1, the direction of a field of view when the operation lever 8 provided in the operation section 3 is operated to be inclined in a direction of arrow Right around the turning axis P from a state where the operation lever 8 is inclined in the direction of arrow U around the turning axis Q (the longitudinal axis of the operation rod is Ku) from the neutral position (the longitudinal axis of the operation rod is Kn) is changed in a leftward direction (from Od to Or).

Figure 27:
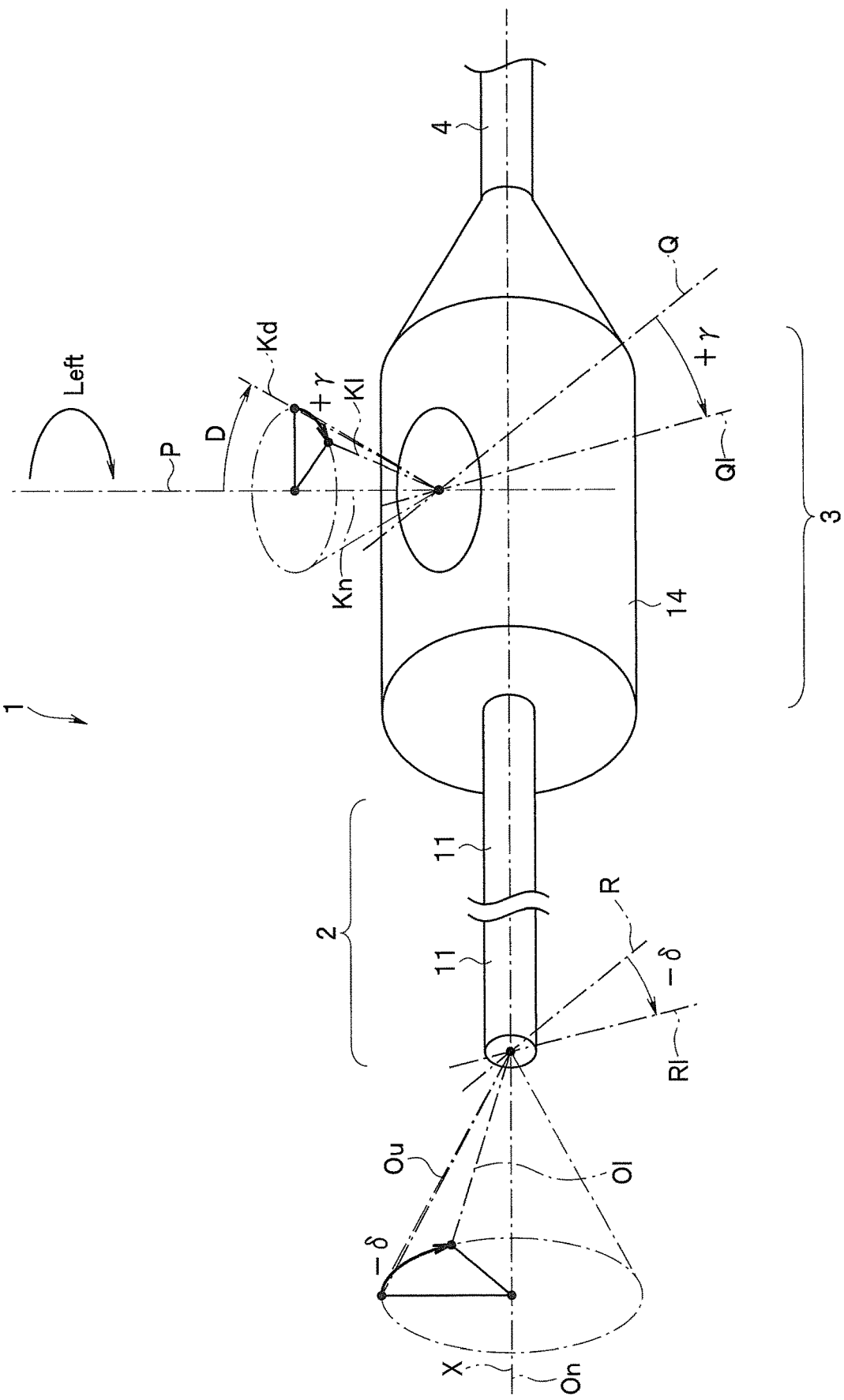
FIG. 27 is a diagram for describing an operation in a state where the operation lever is operated to be inclined leftward with the operation lever operated to be inclined backward according to the modification to the third embodiment.
Figure 28:
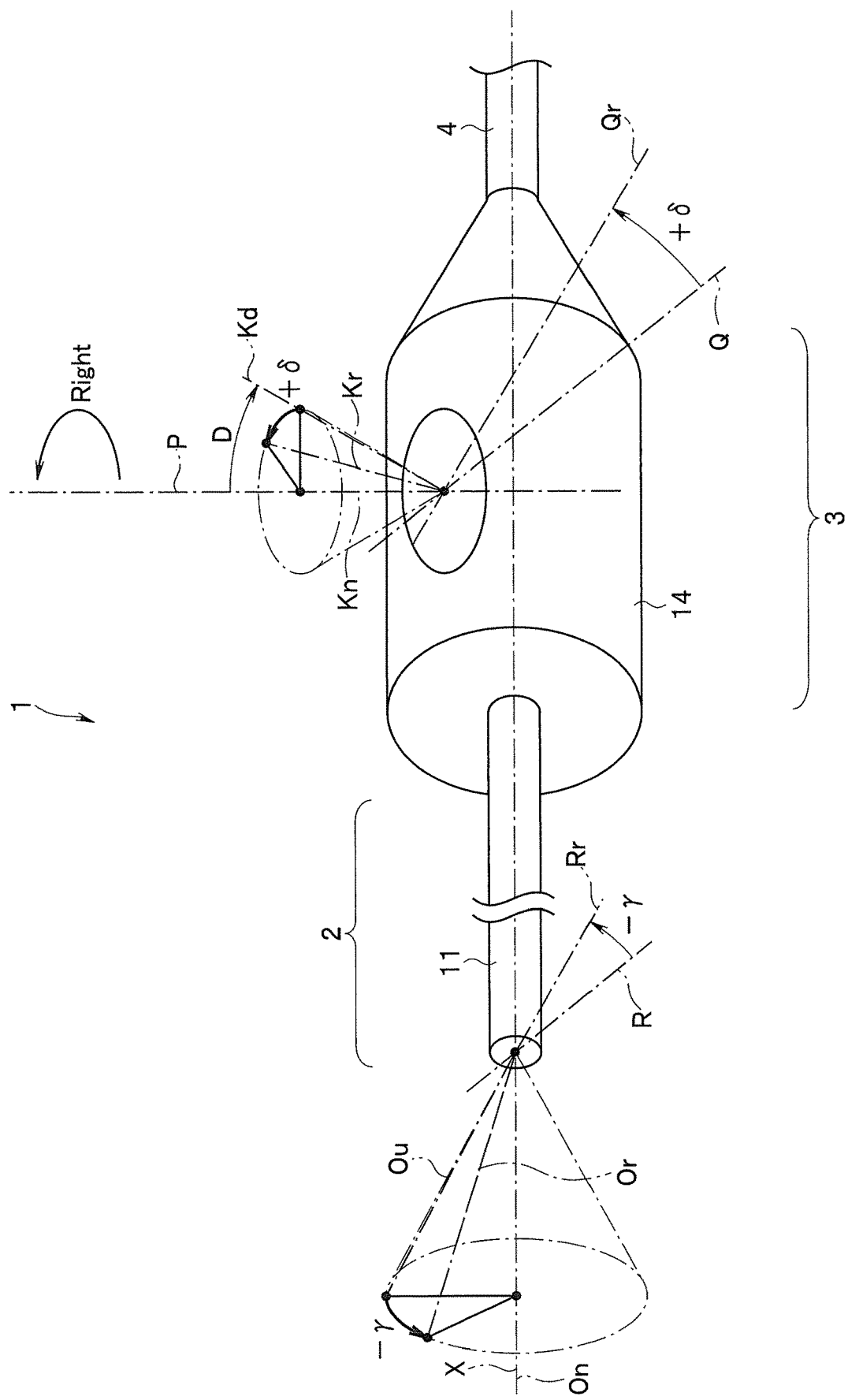
FIG. 28 is a diagram for describing an operation in a state where the operation lever is operated to be inclined rightward with the operation lever operated to be inclined backward according to the modification to the third embodiment.

Similarly, as illustrated in FIGS. 27 and 28, in the endoscope 1, when the operation lever 8 provided in the operation section 3 is operated to be inclined in the direction of arrow Left or the direction of arrow Right around the turning axis P from a state where the operation lever 8 is inclined in the direction of arrow D around the turning axis Q (the longitudinal axis of the operation rod 8a is Kd) from the neutral position (the longitudinal axis of the operation rod is Kn), the direction of a field of view is changed in a leftward or rightward direction (from Ou to Ol or Or), like an operation direction, by a reverse function to the function illustrated in FIGS. 25 and 26.

In other words, in the present modification, a relationship between the operation direction and a field of view change direction is a relationship of an imprint (inverted by 180 degrees) only in an up-and-down direction by a reverse function to the function illustrated in FIGS. 19 to 23. Therefore, the endoscope 1 according to the present embodiment can correspond to the operation direction of the operation lever 8 that suits a user's preference by changing a fixing position of the transmission wire 24.

Therefore, when the present embodiment and the modification to the present embodiment are used, the operation direction and the field of view change direction can be inverted only upward or downward or leftward or rightward, unlike in the first and second embodiments, and can correspond to operation directions of the operation lever 8 that respectively suit a wide variety of user's preferences.

According to each of the above-described embodiments, there can be provided an endoscope having operability improved at the time of change in a field of view because the field of view can be easily varied over a wide range by one operating member for an intended direction and site.

The invention described in each of the above-described embodiments is not limited to the embodiments. In addition, various modifications can be implemented without departing from the scope of the invention in an implementation stage. Further, each of the above-described embodiments includes inventions in various stages, and various inventions can be extracted by an appropriate combination of a plurality of constituent components to be disclosed.

For example, even if some of all the constituent components described in each of the embodiments are deleted, a configuration from which the constituent components are deleted can be extracted as an invention when a described problem can be solved and a described effect is obtained.

The present invention is not limited to the above-described embodiments, but various changes, alterations, and the like are possible without departing from the scope of the present invention.

What is claimed is:

1. An endoscope comprising:
    a rigid insertion section including a first longitudinal axis;
    an operation section provided at a proximal end of the insertion section;
    an optical element disposed in a distal end portion of the insertion section, the optical element configured to rotate around a first axis and around a second axis, the first axis being perpendicular to the first longitudinal axis, the second axis being parallel to the first longitudinal axis,
    an operating lever disposed in the operation section, the operating lever including a second longitudinal axis, the operating lever being turnable around a third axis and turnable around a fourth axis, the third axis and the fourth axis being perpendicular to each other, the fourth axis being parallel to the second longitudinal axis when the operating lever is in a neutral position;
    a turning tube including a tube hole formed along the fourth axis, the operating lever having a portion inserted in the tube hole, the turning tube configured to turn around the fourth axis relative to the operation section in response to a first rotation of the operating lever around the fourth axis;
    a first transmission operatively connecting the optical element to the operating lever, the first transmission configured to convert a second rotation of the operating member around the third axis to a first rotation of the optical element around the first axis; and
    a second transmission configured to convert the first rotation of the operating lever to a second rotation of the optical element around the second axis.

2. The endoscope according to claim 1, wherein the second transmission comprises gears configured to turn in response to the first rotation of the operating member.

3. The endoscope according to claim 2, wherein the gears comprise one or more of a spur gear and a bevel gear.

4. The endoscope according to claim 1, wherein the second transmission comprises one or more pulleys and one or more belts, and turning of the one or more pulleys is transmitted with the one or more belts.

5. The endoscope according to claim 1, wherein the second transmission comprises a flexible shaft.

6. The endoscope according to claim 1, wherein the second axis and an axis obtained by projecting the fourth axis on a plane parallel to the fourth axis and including the second axis cross each other at a predetermined angle.

7. The endoscope according to claim 6, wherein the predetermined angle is optionally settable within a range of 0 degrees to 90 degrees.

8. The endoscope according to claim 1, wherein a turning angle around the first axis of the optical element is less than 180 degrees.

9. The endoscope according to claim 1, wherein a turning angle of the second rotation is less than 180 degrees.

10. The endoscope according to claim 1, wherein the second transmission is configured to rotate the optical element around the second axis in response to the first rotation in a state when the lever is pivoted around the third axis from the neutral position in response to the first rotation.

11. The endoscope according to claim 1, wherein the rigid insertion section includes an exterior tube forming the exterior of the rigid insertion section, the exterior tube being rotatably connected to the operation portion and configured to be rotated around the second axis by the second transmission relative to the operation section in response to the first rotation.

12. The endoscope according to claim 1, wherein the first transmission comprises:
    a wire having a first end at least indirectly connected to a frame holding the optical element and a second end at least indirectly connected to the operating lever;
    wherein the first end is at least indirectly connected to the frame at a first distance from the first axis and the second end is at least indirectly connected to the operating lever at a second distance from the third axis.

13. The endoscope according to claim 1, wherein the second axis is coincident with the first longitudinal axis.

14. The endoscope according to claim 1, wherein the fourth axis is coincident with the second longitudinal axis.

15. An endoscope comprising:
    a rigid insertion section including a first longitudinal axis;
    an operation section provided at a proximal end of the insertion section;
    an optical element disposed in a distal end portion of the insertion section, the optical element configured to rotate around a first axis and around a second axis, the first axis being offset from the first longitudinal axis, the second axis being parallel to the first longitudinal axis,
    an operating lever disposed in the operation section, the operating lever including a second longitudinal axis, the operating lever being turnable around a third axis and turnable around a fourth axis, the third axis and the fourth axis being offset from each other, the fourth axis being parallel to the second longitudinal axis when the operating lever is in a neutral position;
    a turning body including a cavity formed along the fourth axis, the operating lever having a portion inserted in the cavity, the turning body configured to turn around the fourth axis relative to the operation section in response to a first rotation of the operating lever around the fourth axis;
    a first transmission operatively connecting the optical element to the operating lever, the first transmission configured to convert a second rotation of the operating member around the third axis to a first rotation of the optical element around the first axis; and
    a second transmission configured to convert the first rotation of the operating lever to a second rotation of the optical element around the second axis.

16. The endoscope according to claim 15, wherein the first axis is perpendicular to the first longitudinal axis.

17. The endoscope according to claim 15, wherein the third axis is perpendicular to the fourth longitudinal axis.

18. The endoscope according to claim 15, wherein the turning body is a turning tube and the cavity is a tube hole.

19. An endoscope comprising:
   a rigid insertion section including a first longitudinal axis;
   an operation section provided at a proximal end of the insertion section;
   an optical element disposed in a distal end portion of the insertion section, the optical element configured to rotate around a first axis and around a second axis, the first axis being perpendicular to the first longitudinal axis, the second axis being parallel to the first longitudinal axis,
   an operating lever disposed in the operation section, the operating lever including a second longitudinal axis, the operating lever being turnable around a third axis and turnable around a fourth axis, the third axis and the fourth axis being perpendicular to each other, the fourth axis being parallel to the second longitudinal axis when the operating lever is in a neutral position;
   a first transmission operatively connecting the optical element to the operating lever, the first transmission configured to convert a first rotation of the operating member around the third axis to a first rotation of the optical element around the first axis; and
   a second transmission configured to convert a second rotation of the operating lever around the fourth axis to a second rotation of the optical element around the second axis.

20. The endoscope according to claim 19, further comprising a turning tube including a tube hole formed along the fourth axis, the operating lever having a portion inserted in the tube hole, the turning tube configured to turn around the fourth axis relative to the operation section in response to the second rotation of the operating lever around the fourth axis.

* * * * *